(12) United States Patent
Rodriguez et al.

(10) Patent No.: US 12,336,746 B2
(45) Date of Patent: Jun. 24, 2025

(54) SCREW INSERTER INSTRUMENTS AND METHODS

(71) Applicant: Medos International Sarl, Le Locle (CH)

(72) Inventors: Joshua Rodriguez, East Providence, RI (US); Daniel Moreno, Bridgewater, MA (US); Nicholas Pavento, North Attleboro, MA (US); Keanan R. Smith, Quincy, MA (US); James Murray, Quincy, MA (US); Eric Biester, Barrington, RI (US)

(73) Assignee: Medos International Sàrl, Le Locle (CH)

( * ) Notice: Subject to any disclaimer, the term of this patent is extended or adjusted under 35 U.S.C. 154(b) by 441 days.

(21) Appl. No.: 17/557,137

(22) Filed: Dec. 21, 2021

(65) Prior Publication Data

US 2022/0110666 A1 Apr. 14, 2022

Related U.S. Application Data

(63) Continuation of application No. 16/440,618, filed on Jun. 13, 2019, now Pat. No. 11,224,472.

(51) Int. Cl.
*A61B 17/70* (2006.01)
*A61B 17/88* (2006.01)
*A61B 17/00* (2006.01)

(52) U.S. Cl.
CPC ...... *A61B 17/8886* (2013.01); *A61B 2017/00407* (2013.01); *A61B 2017/00477* (2013.01)

(58) Field of Classification Search
CPC ............ A61B 17/7082; A61B 17/88–17/8891
See application file for complete search history.

(56) References Cited

U.S. PATENT DOCUMENTS 2,512,232 A  6/1950 Hart
4,770,071 A  9/1988 Steier
(Continued)

FOREIGN PATENT DOCUMENTS

CN  107106215 B  3/2020
JP  H07163599 A  6/1995
(Continued)

OTHER PUBLICATIONS

International Search Report and Written Opinion received for PCT Application No. PCT/EP2020/066027, mailed on Oct. 15, 2020, 17 pages.
(Continued)

*Primary Examiner* — Zade Coley
(74) *Attorney, Agent, or Firm* — Barnes & Thornburg LLP

(57) ABSTRACT

Screw inserter instruments and methods for implanting a bone screw are disclosed herein. In one exemplary embodiment, a screw inserter instrument can include a screw drive assembly having a first handle and a driver shaft coupled to the first handle, and a stylet assembly having a second handle and a stylet extending through the driver shaft. The first handle can have a locked configuration, in which the first handle and the driver shaft are coupled such that the first handle can maintain the driver shaft in a fixed position while the second handle is rotated relative to the first handle, and an unlocked configuration, in which the first handle and the driver shaft can rotate simultaneously in a first direction and the first handle can rotate independent of the driver shaft in a second opposite direction.

16 Claims, 17 Drawing Sheets

(56) References Cited

U.S. PATENT DOCUMENTS

| | | | |
|---|---|---|---|
| 5,613,585 A | 3/1997 | Tiede | |
| 6,019,776 A | 2/2000 | Preissman et al. | |
| 6,402,757 B1 | 6/2002 | Moore, III et al. | |
| 6,827,722 B1* | 12/2004 | Schoenefeld | A61B 17/1622 606/88 |
| 6,981,974 B2 | 1/2006 | Berger | |
| 7,207,995 B1* | 4/2007 | Vandewalle | A61B 17/8875 606/104 |
| 7,338,494 B2 | 3/2008 | Ryan | |
| 7,488,323 B2 | 2/2009 | Bacastow et al. | |
| 7,604,643 B2 | 10/2009 | Ciccone et al. | |
| 7,621,918 B2* | 11/2009 | Jackson | A61B 17/7002 606/104 |
| 7,892,207 B2 | 2/2011 | Simonton et al. | |
| 7,938,836 B2 | 5/2011 | Ainsworth et al. | |
| 8,192,466 B2 | 6/2012 | Yue et al. | |
| 8,216,243 B2* | 7/2012 | Yevmenenko | A61B 17/8886 606/104 |
| 8,236,006 B2 | 8/2012 | Hamada | |
| 8,282,651 B2 | 10/2012 | Ciccone et al. | |
| 8,303,601 B2 | 11/2012 | Bandeira et al. | |
| 8,372,076 B2 | 2/2013 | Simonton et al. | |
| 8,394,108 B2 | 3/2013 | McLean et al. | |
| 8,603,094 B2* | 12/2013 | Walker | A61B 17/7086 606/86 A |
| 8,845,640 B2* | 9/2014 | McLean | A61B 17/7086 606/86 A |
| 9,265,548 B2 | 2/2016 | Jones et al. | |
| 9,295,500 B2* | 3/2016 | Marigowda | A61B 17/7082 |
| 9,855,087 B2* | 1/2018 | Divincenzo | A61B 17/7082 |
| 10,085,786 B2 | 10/2018 | Chandanson et al. | |
| 10,433,883 B2* | 10/2019 | DiVincenzo | A61B 17/1604 |
| 10,568,677 B2* | 2/2020 | DiVincenzo | A61B 17/7091 |
| 10,779,872 B2* | 9/2020 | Smith | A61B 17/864 |
| 11,123,113 B2 | 9/2021 | Rodriguez et al. | |
| 11,224,472 B2 | 1/2022 | Rodriguez et al. | |
| 2005/0216027 A1 | 9/2005 | Suh et al. | |
| 2006/0069391 A1* | 3/2006 | Jackson | A61B 17/7001 606/62 |
| 2006/0195017 A1* | 8/2006 | Shluzas | A61B 17/7083 600/210 |
| 2007/0016219 A1* | 1/2007 | Levine | A61B 90/39 606/99 |
| 2007/0043378 A1* | 2/2007 | Kumar | A61B 17/7082 606/104 |
| 2008/0045970 A1* | 2/2008 | Saidha | A61B 17/7035 81/436 |
| 2008/0147128 A1 | 6/2008 | Fritzinger | |
| 2009/0163963 A1* | 6/2009 | Berrevoets | A61B 17/8875 606/104 |
| 2009/0275954 A1 | 11/2009 | Phan et al. | |
| 2009/0275994 A1* | 11/2009 | Phan | B25B 23/101 606/103 |
| 2010/0198272 A1* | 8/2010 | Keyer | A61B 17/7037 606/305 |
| 2010/0211115 A1* | 8/2010 | Tyber | A61B 17/863 606/305 |
| 2010/0241124 A1 | 9/2010 | Housman et al. | |
| 2011/0015678 A1* | 1/2011 | Jackson | A61B 17/7088 606/264 |
| 2011/0054537 A1 | 3/2011 | Miller et al. | |
| 2011/0313476 A1* | 12/2011 | McLean | A61B 17/7086 606/86 A |
| 2013/0012954 A1 | 1/2013 | Paroth et al. | |
| 2014/0039567 A1 | 2/2014 | Hoefer et al. | |
| 2014/0276894 A1* | 9/2014 | Ramsay | A61B 17/8897 606/104 |
| 2014/0324062 A1* | 10/2014 | Heuer | B25B 23/101 606/104 |
| 2015/0201987 A1 | 7/2015 | Lemoine et al. | |
| 2016/0030100 A1* | 2/2016 | Divincenzo | A61B 17/7082 606/104 |
| 2016/0262809 A1 | 9/2016 | May et al. | |
| 2016/0296266 A1 | 10/2016 | Chandanson et al. | |
| 2018/0014858 A1 | 1/2018 | Biester et al. | |
| 2018/0014862 A1 | 1/2018 | Raina et al. | |
| 2018/0110553 A1* | 4/2018 | DiVincenzo | A61B 17/7091 |
| 2018/0353224 A1* | 12/2018 | Kam | A61B 17/7082 |
| 2018/0368893 A1* | 12/2018 | DiVincenzo | A61B 17/1604 |
| 2019/0125421 A1* | 5/2019 | Smith | A61B 17/8897 |
| 2020/0390484 A1 | 12/2020 | Emil et al. | |

FOREIGN PATENT DOCUMENTS

| | | |
|---|---|---|
| JP | 2015173984 A | 10/2015 |
| JP | 2016509488 A | 3/2016 |
| JP | 2016511064 A | 4/2016 |
| WO | 2014082087 A1 | 5/2014 |
| WO | 2018013607 A1 | 1/2018 |

OTHER PUBLICATIONS

International Search Report and Written Opinion received for PCT Application No. PCT/EP2020/066043, mailed on Nov. 2, 2020, 22 pages.

Chinese First Office Action for Application No. 202080043290.1 dated Apr. 11, 2025 (26 pages).

Chinese First Office Action for Application No. 202080043221.0, dated Apr. 14, 2025 (32 pages).

* cited by examiner

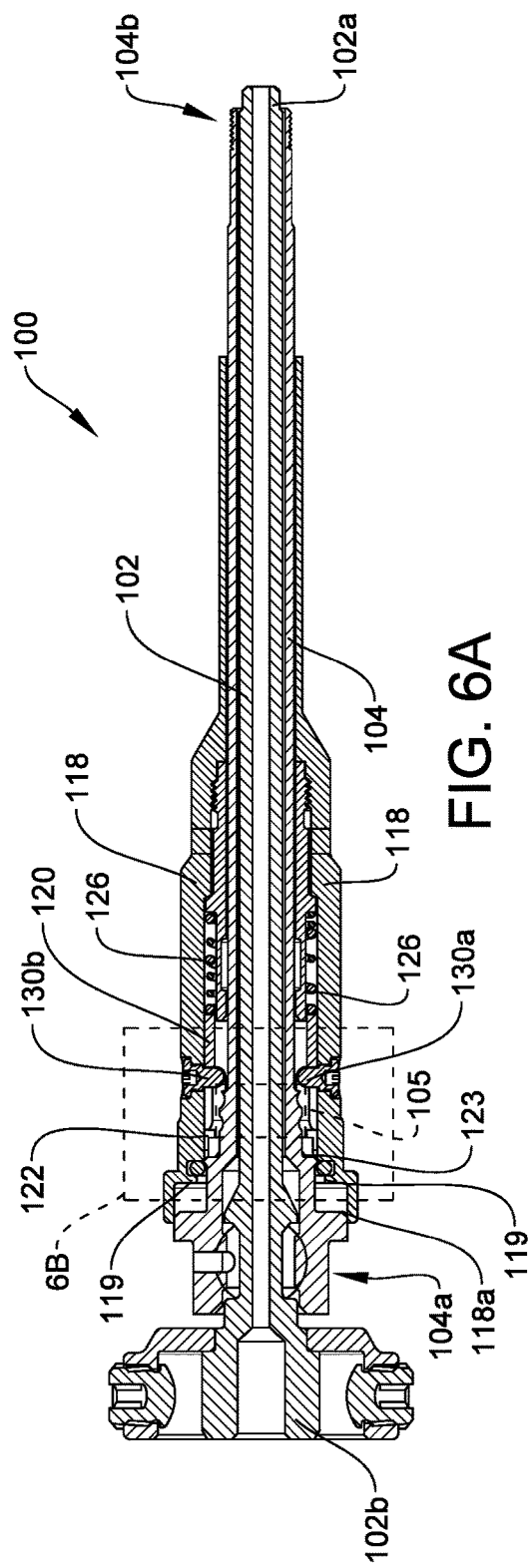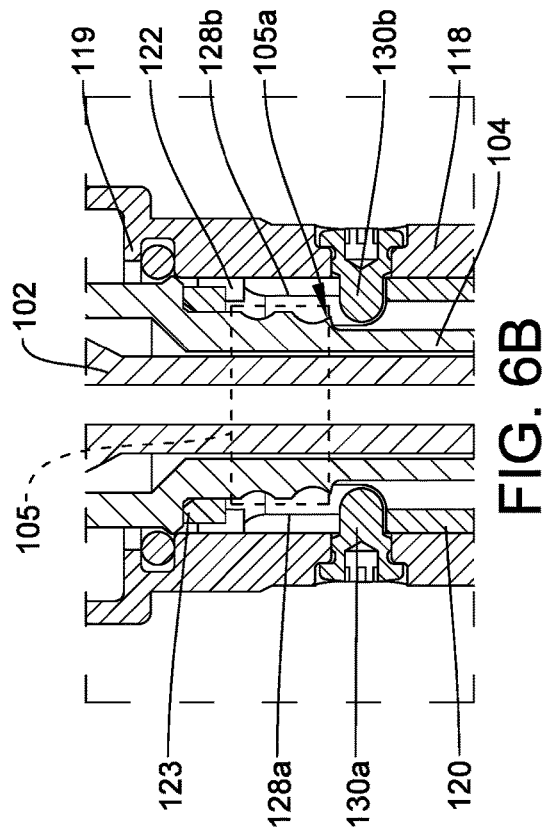
FIG. 6A
FIG. 6B

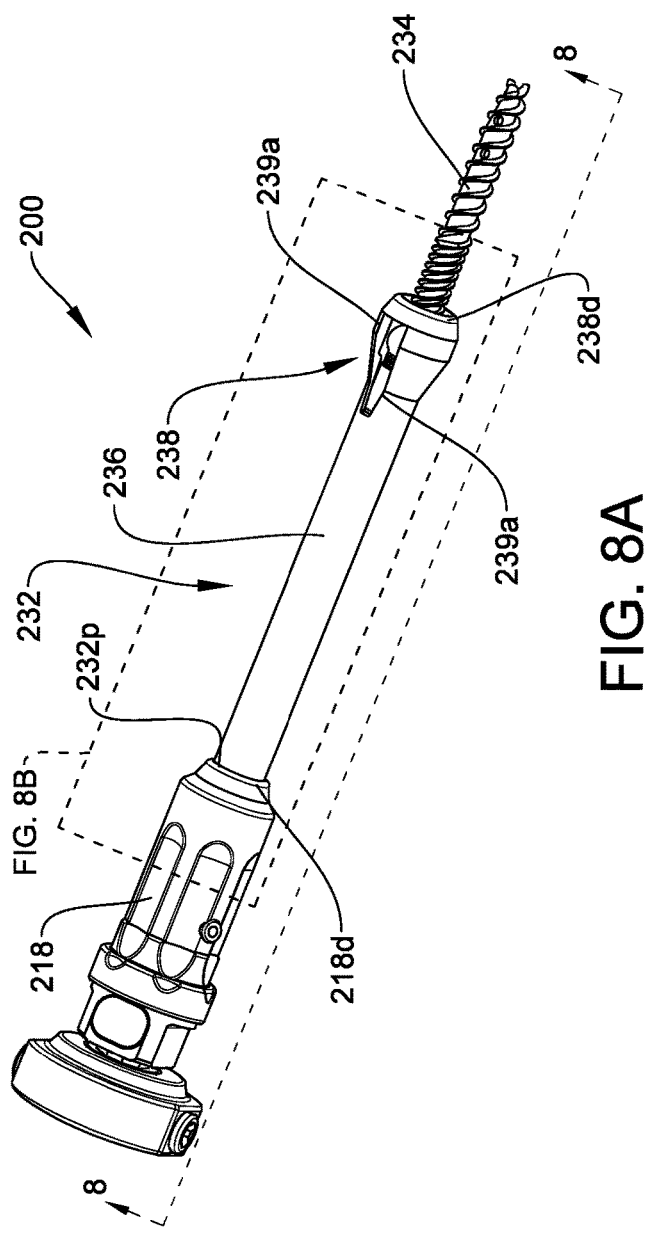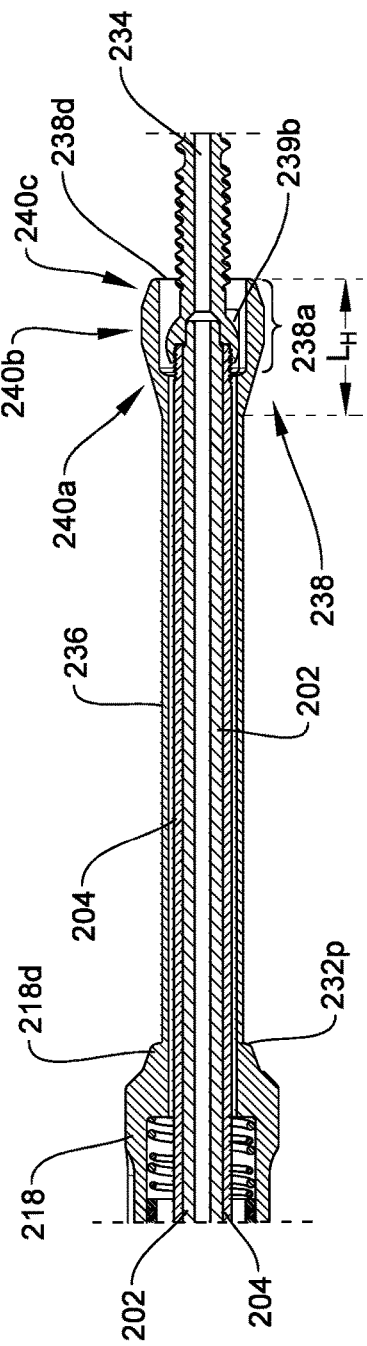
FIG. 8A
FIG. 8B

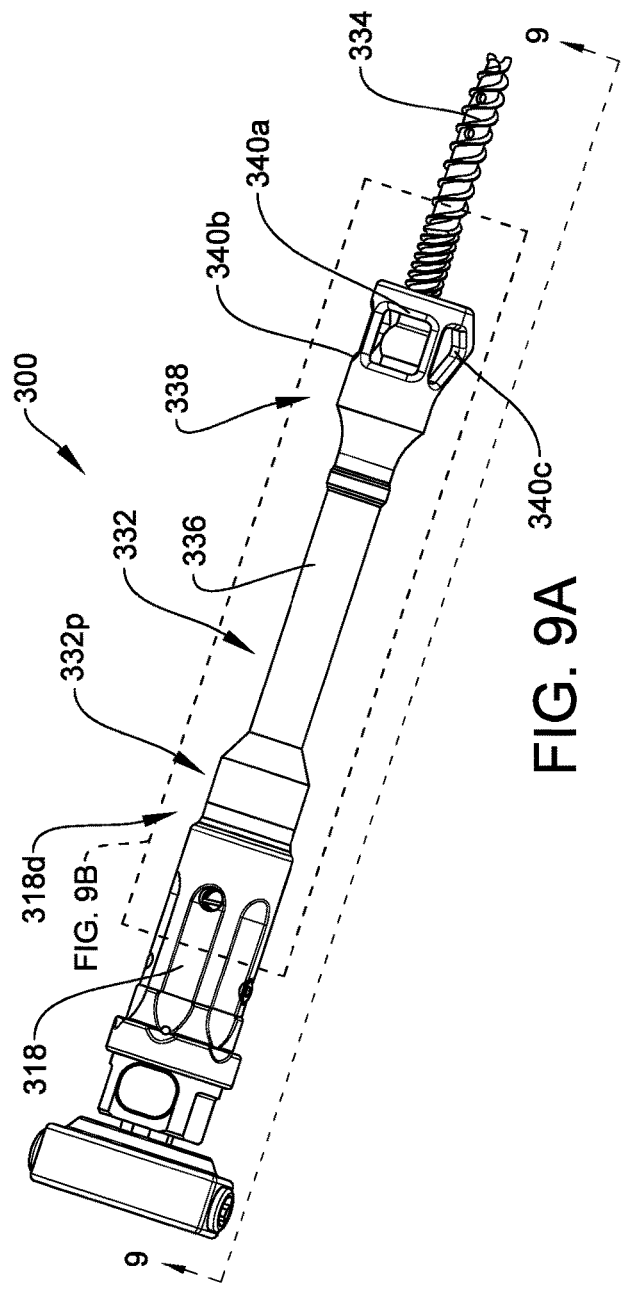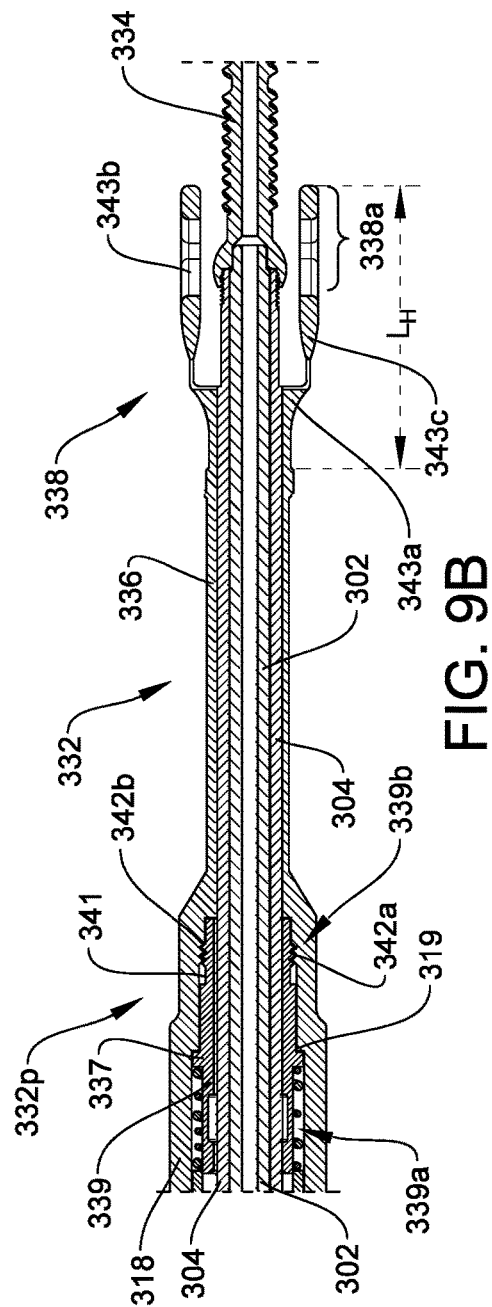

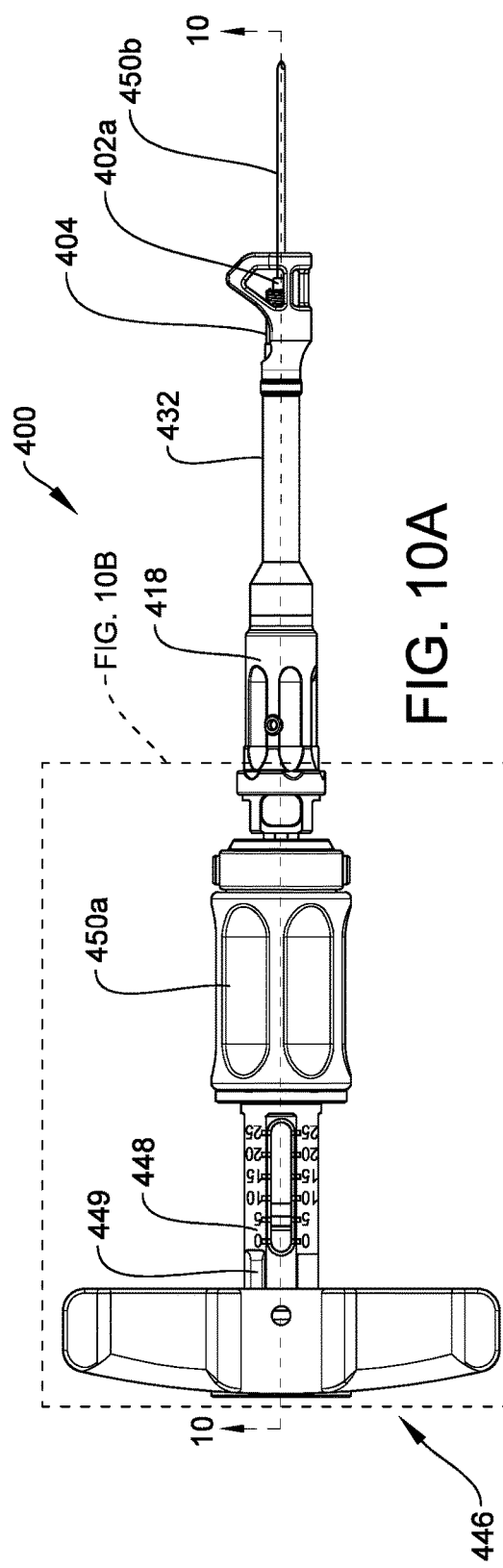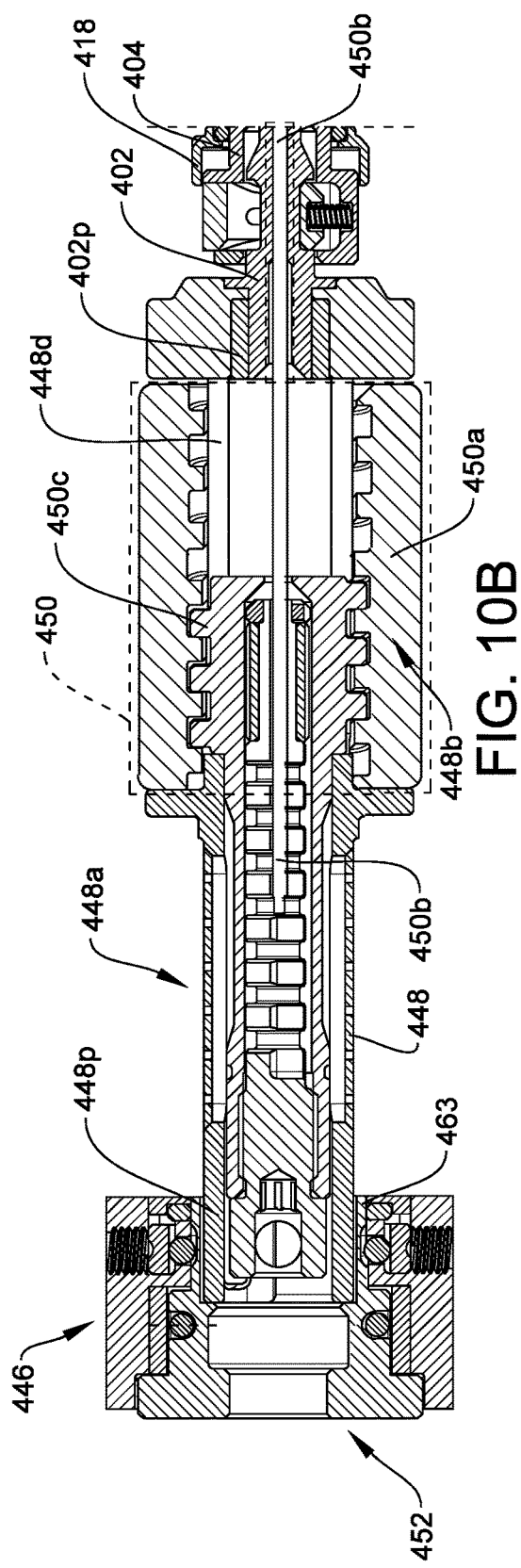

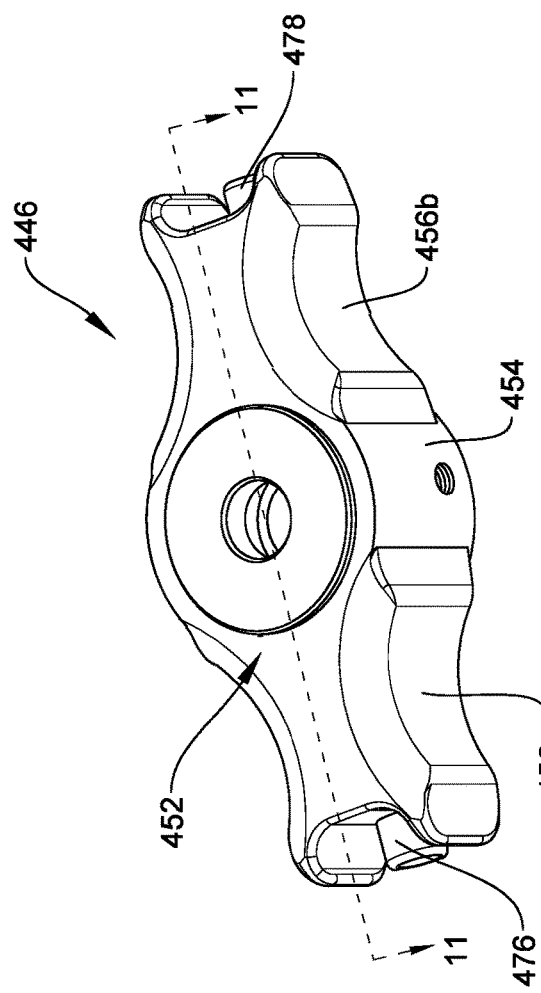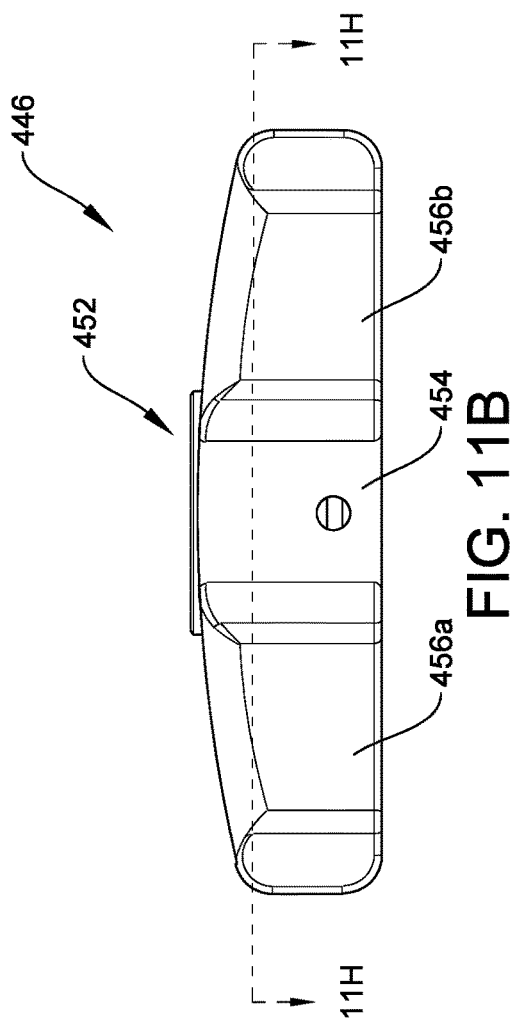
FIG. 11A
FIG. 11B

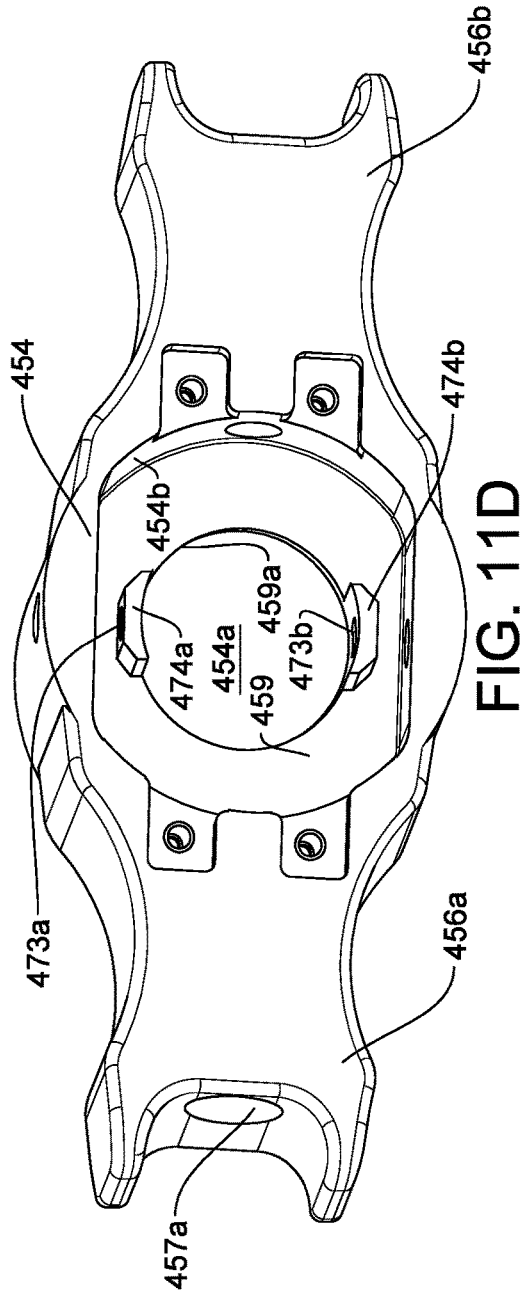
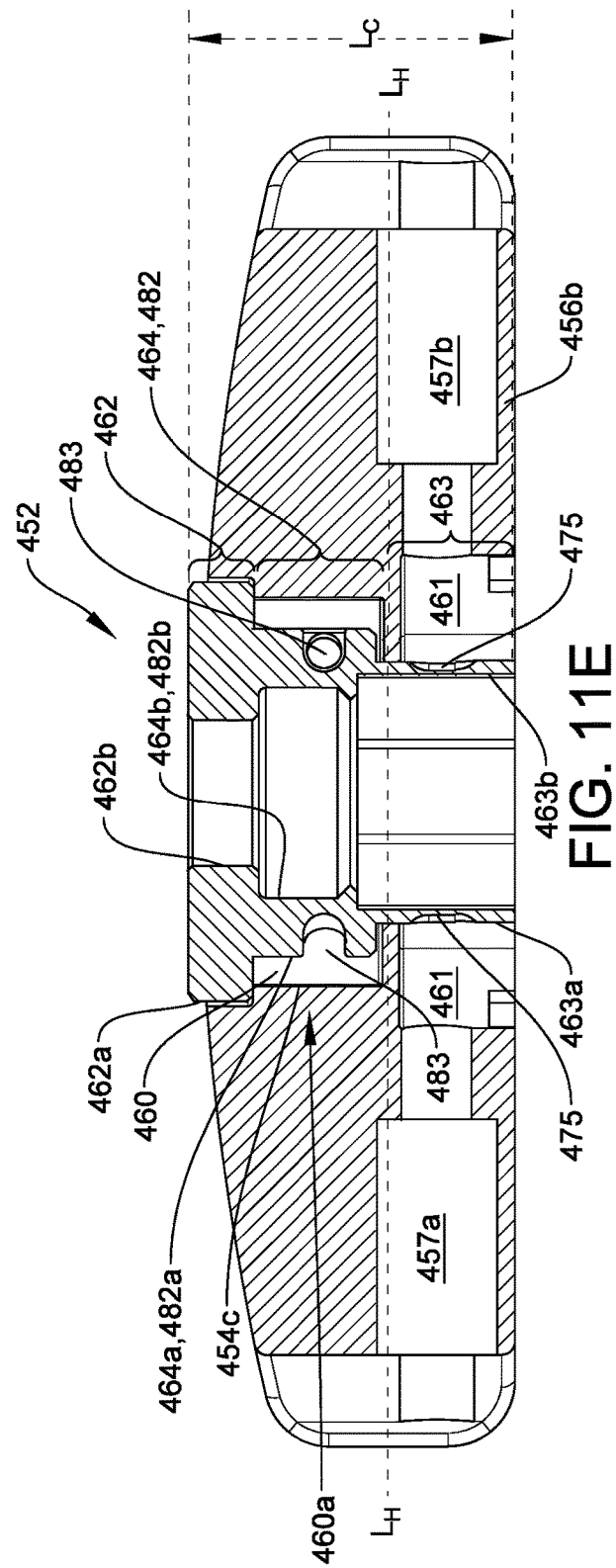
FIG. 11D
FIG. 11E

SCREW INSERTER INSTRUMENTS AND METHODS

CROSS-REFERENCE TO RELATED APPLICATIONS

This application is a continuation of U.S. patent application Ser. No. 16/440,618 filed on Jun. 13, 2019 and entitled "Screw Inserter Instrument and Methods," the entire contents of which are hereby incorporated herein by its references to its entirety.

FIELD

Screw inserter instruments and methods are disclosed herein.

BACKGROUND

Bone screws, such as pedicle screws, can be used in orthopedic surgery to fix bone during healing, fusion, or other processes. In spinal surgery, for example, bone screws can be used to secure a spinal fixation element to one or more vertebrae to rigidly or dynamically stabilize the spine.

Conventional posterior pedicle screw fixation requires that the pedicle screw be prepared via awling, probing, and tapping prior to insertion. While advancements have been made that allow the insertion of pre-assembled pedicle screws, these systems are not ideal for placement of all screws in a construct prior to transforaminal lumbar interbody fusion (TLIF). This is due to obstruction of the visual field by the pre-assembled heads of the pedicle screws.

When inserting most pedicle screws, the screw must be retained in some fashion to the screw inserter instrument. This is typically accomplished by threading a sleeve into either the polyaxial head of the screw, or in the case of modular screws, into a collet coupled thereto. In use, the user holds the sleeve stationary, as a result, the act of driving the screw into bone also unthreads the sleeve from the screw before the screw is completely inserted in bone. Clinically, this can cause delays as the surgeon must then re-engage the screw to finish implantation. This reengagement can be challenging, particularly where direct visualization of the screw is compromised.

During a minimally invasive procedure, it can be difficult for the surgeon to directly visualize the screw as it is being driven into bone. As a result, it can be visually challenging to determine the insertion depth of the screw, which can lead to incomplete implantation of the screw, or alternatively, over insertion of the screw. For example, when using a modular screw, the screw can be driven too far into bone such that the length of screw extending outward from the bone is insufficient for proper attachment of the polyaxial head to the screw.

Screw inserter instruments are available having a stylet protruding therefrom. The stylet can be docked into bone by tapping or urging the instrument distally towards bone. Once the stylet is advanced to the desired depth, a coupled bone screw is driven along the path created by the stylet while the stylet is retracted therefrom. To prevent the coupled bone screw from being inserted into or removed from bone during stylet advancement and retraction, a user must maintain the instrument's screw driver handle in a stationary position. However, this can be difficult and may interfere with advancement and retraction of the stylet.

Accordingly, despite existing technologies, there remains a need for improved instrumentation and methods associated with driving bone screws into bone.

SUMMARY

Various screw inserter instruments and methods are disclosed for implanting a bone screw or a bone screw assembly into bone.

In one embodiment, a screw inserter instrument is provided and includes a screw drive assembly having a first handle and a driver shaft coupled to the first handle, and a stylet assembly having a second handle and a stylet extending through the driver shaft. The driver shaft can have a distal tip configured to couple to a bone screw for driving the bone screw into bone. The first handle can have a locked configuration in which the first handle and the driver shaft are coupled such that the first handle can maintain the driver shaft in a fixed position while the second handle is rotated relative to the first handle, and an unlocked configuration in which the first handle and the driver shaft can rotate simultaneously in a first direction and the first handle can rotate independent of the driver shaft in a second opposite direction. In one embodiment, the first handle can be biased to the locked configuration.

In some embodiments, the screw inserter instrument can include a control mechanism disposed within the first handle and in communication with the driver shaft. The control mechanism can have a variety configurations. For example, in some embodiments, the control mechanism can include at least one trigger element that can be fixedly coupled to a locking ring such that movement of the at least one trigger element can move the locking ring to cause the first handle to move between the locked configuration and the unlocked configuration. In one embodiment, when the first handle is in the locked configuration, the locking ring can be operably coupled to the driver shaft such that the first handle and the driver shaft are locked together. In another embodiment, when the first handle is in the unlocked configuration, the locking ring can be operably decoupled from the driver shaft such that the first handle and the driver shaft rotate independent of each other.

In other embodiments, the screw inserter instrument can include a ratchet mechanism disposed within the first handle. The ratchet mechanism can have a variety of configurations. In one embodiment, the ratchet mechanism can allow bidirectional rotation of the first handle to unidirectionally drive the driver shaft to drive a bone screw into bone when the first handle is in the unlocked configuration.

In some embodiments, the screw inserter instrument can include a retaining sleeve disposed around the driver shaft. The retaining sleeve can have a distal end configured to threadably engage with a bone screw. In one embodiment, when the first handle is in the locked configuration, the first handle can maintain the driver shaft in a stationary position while the retaining sleeve can be rotated to threadably disengage from the bone screw, and when the first handle is in the unlocked configuration, the second handle can be held stationary while the first handle can be rotated in the first direction to rotate the driver shaft and retaining sleeve together to drive the bone screw into bone.

In another exemplary embodiment, a screw inserter instrument is provided having a screw drive assembly that includes a handle and a driver shaft operatively coupled to the handle, a locking assembly within the handle and in communication with the driver shaft, and a clutch assembly in communication with the handle and the driver shaft. The driver shaft can have a distal tip configured to couple to a bone screw for driving the bone screw into bone. The locking assembly can have a locked configuration in which the handle and the driver shaft are locked to one another such that they rotate as a unit, and an unlocked configuration in which the handle and the driver shaft rotate independent of each other. The clutch assembly can be configured, when the locking assembly is in the unlocked configuration, to allow the handle to rotate in first and second opposite directions to drive the driver shaft in only the first direction. In one embodiment, the locking assembly can be biased to the locked configuration.

The locking assembly can have a variety of configurations. For example, in some embodiments, the locking assembly can include at least one trigger element that can be fixedly coupled to a locking ring such that movement of the at least one trigger element can move the locking ring to cause the locking assembly to move between the locked and unlocked configurations. In one embodiment, when the locking assembly is in the locked configuration, the locking ring can be operably coupled to the driver shaft such that the handle and the driver shaft are locked together. In another embodiment, when the locking assembly is in the unlocked configuration, the locking ring can be operably decoupled from the driver shaft such that the handle and the driver shaft rotate independent of each other.

The clutch assembly can have a variety of configurations. For example, in some embodiments, the clutch assembly can include inner and outer rings that can be selectively engaged to each other such that rotation of the handle in the first direction is effective to cause rotation of the driver shaft only when the first and second inner and outer rings are engaged.

In some embodiments, the screw inserter instrument can include a retaining sleeve disposed around the driver shaft. The retaining sleeve can have a distal end configured to threadably engage with the bone screw. In one embodiment, when the locking assembly is in the locked configuration, the driver shaft can be held stationary while the retaining sleeve can rotate to threadably disengage from the bone screw, and when the locking assembly is in the unlocked configuration, the locking sleeve can be held stationary while the handle can be rotated in the first direction to rotate the driver shaft and retaining sleeve together to drive the bone screw into bone.

Method for implanting a bone screw are also provided. In one exemplary embodiment, the method can include moving an actuator on a first handle on a screw inserter instrument to switch the first handle from a locked configuration to an unlocked configuration thereby decoupling the first handle from a driver shaft on the screw inserter instrument. The driver shaft can have a distal tip that is coupled to a bone screw. The method can also include rotating the first handle in first and second directions while holding a second handle on the screw inserter instrument stationary to cause the first handle to drive the driver shaft in only the first direction and thereby drive the bone screw into bone.

In some embodiments, rotating the first handle in the first direction can cause a clutch assembly to couple the first handle to the driver shaft. The clutch assembly can prevent rotation of the driver shaft in the second direction when the first handle is rotated in the second direction. In other embodiments, moving the actuator to switch the first handle from the locked configuration to the unlocked configuration can cause a locking ring in the first handle to move from a first position, in which the locking ring is operably coupled to the first handle and the driver shaft, to a second position, in which the locking ring is operably decoupled from the driver shaft.

In other embodiments, the method can include rotating the second handle, prior to moving the actuator on the first handle, while holding the first handle stationary to axially translate a stylet coupled to the second handle and extending through the bone screw to thereby adjust an axial position of the stylet relative to the bone screw.

BRIEF DESCRIPTION OF THE DRAWINGS

This invention will be more fully understood from the following detailed description taken in conjunction with the accompanying drawings, in which:

FIG. 6A is a cross-sectional view of the screw inserter instrument of FIG. 1A taken at 6-6 which is rotated 90 degrees from the cross-section view of FIG. 3;

FIG. 6B is a magnified cross-sectional view of a portion of the screw inserter instrument of FIG. 6A taken at 6B;

FIG. 8A is a perspective view of another embodiment of a screw inserter instrument that includes a driver shaft, a retaining sleeve, a locking sleeve, and a stop sleeve, showing the instrument coupled to a bone screw;

FIG. 8B is a cross-sectional magnified view of a portion of the screw inserter instrument of FIG. 8A taken at 8B-8B;

FIG. 9A is a perspective view of another embodiment of a screw inserter instrument that includes a driver shaft, a retaining sleeve, a locking sleeve, and a stop sleeve, showing the instrument coupled to a bone screw;

FIG. 9B is a cross-sectional view of a portion of the screw inserter instrument of FIG. 9A taken at 9B-9B;

FIG. 10A is a side view of one embodiment of a screw inserter instrument that includes a first handle, a driver shaft, a stylet assembly, a retaining sleeve, a locking sleeve, and a stopping sleeve;

FIG. 10B is a cross-sectional view of the screw inserter instrument of FIG. 10A taken at 10-10;

FIG. 11A is perspective view of a first handle of FIG. 10A;

FIG. 11B is side view of the first handle of FIG. 11A.

FIG. 11D is a perspective view of the first handle of FIG. 11A, showing only a base member;

FIG. 11E is a cross-sectional view of the first handle of FIG. 11A taken at 11-11, showing only a base member and a coupling member;

DETAILED DESCRIPTION

Figure 1A:
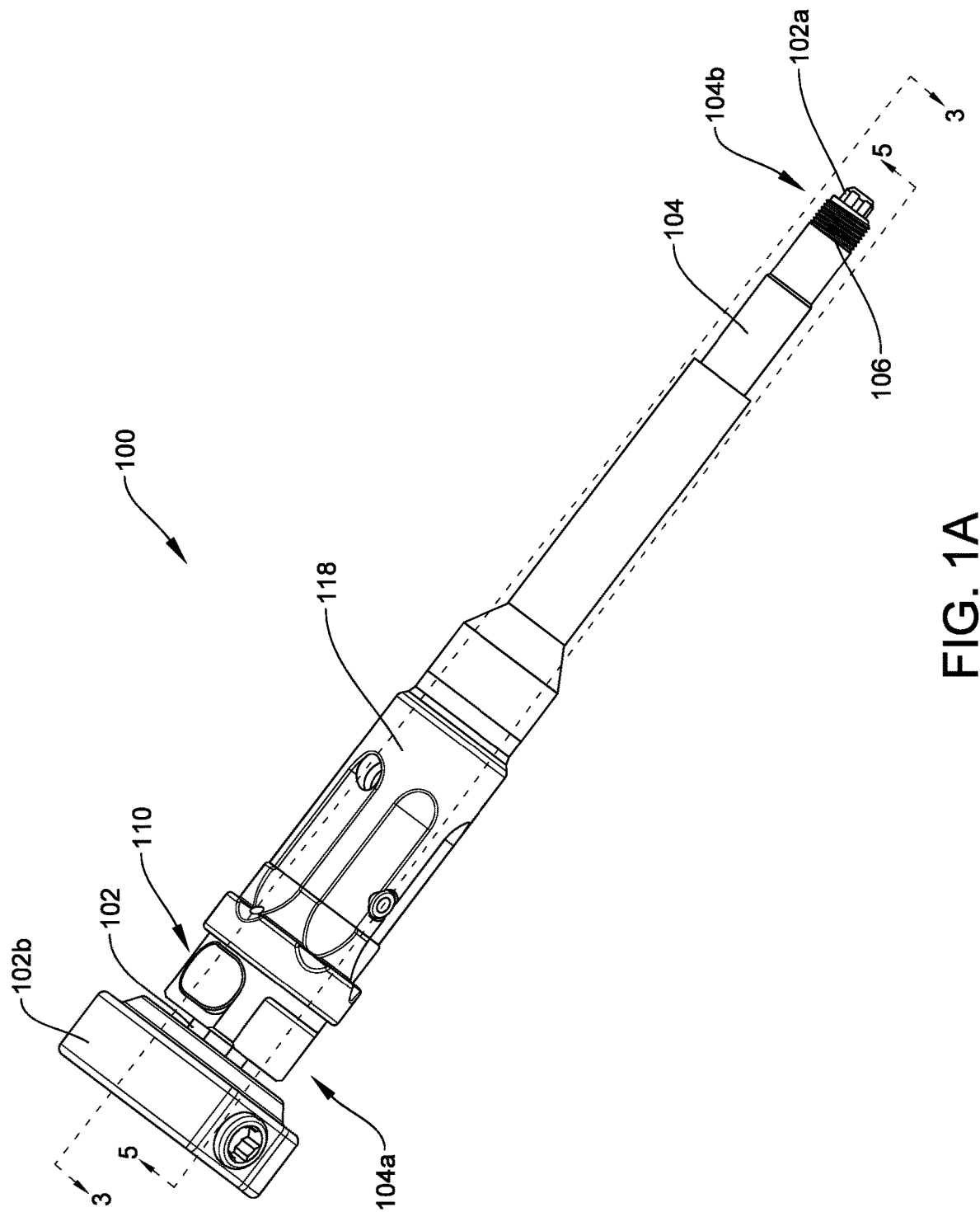
FIG. 1A is a perspective view of one embodiment of a screw inserter instrument that includes a driver shaft, a retaining sleeve, and a locking sleeve, showing the locking sleeve in a first or disengaged position.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various surgical instruments and methods are provided for driving a bone screw or bone screw assembly into bone. In some embodiments, the instruments and methods allow for maintaining a connection between the bone screw and the instrument while the bone screw is being driven into bone. This connection can help control the alignment of the bone screw, and thus decrease toggling, during insertion. As a result, the bone screw can be more accurately inserted along an intended pathway within the bone. Alternatively, or in addition, the instruments and methods can be designed to provide tactile feedback once a screw has reached a desired insertion depth within bone (e.g., an insertion depth associated with a sufficient length of screw needed for polyaxial head assembly). This tactile feedback can allow for controlled screw insertion such that, for example, a user can avoid driving a screw too far into bone. Further, in other embodiments, the instruments and methods can be designed to allow a surgeon to drive a screw into bone using a ratcheting mechanism, thus allowing the surgeon to keep his/her hand in engagement with the instrument. As a result, the surgeon has more finite control during screw insertion.

An exemplary screw inserter instrument can include a variety of features to facilitate implantation of a bone screw, as described herein and illustrated in the drawings. However, a person skilled in the art will appreciate that the screw inserter instruments can include only some of these features and/or can include a variety of other features known in the art. The screw inserter instruments described herein are merely intended to represent certain exemplary embodiments.

FIGS. 1A-7B illustrate an exemplary embodiment of a screw inserter instrument 100 that is configured to prevent decoupling of a retaining sleeve from a bone screw when driving the bone screw into bone. The illustrated screw inserter instrument 100 generally includes a driver shaft 102, a retaining sleeve 104 disposed around the driver shaft 102, and a locking sleeve 118. The retaining sleeve 104 and the locking sleeve 118 are collectively referred to herein as a sleeve assembly. For purposes of simplicity, certain components of the screw inserter instrument 100 are not illustrated in FIGS. 1A-7B.

Figure 2:
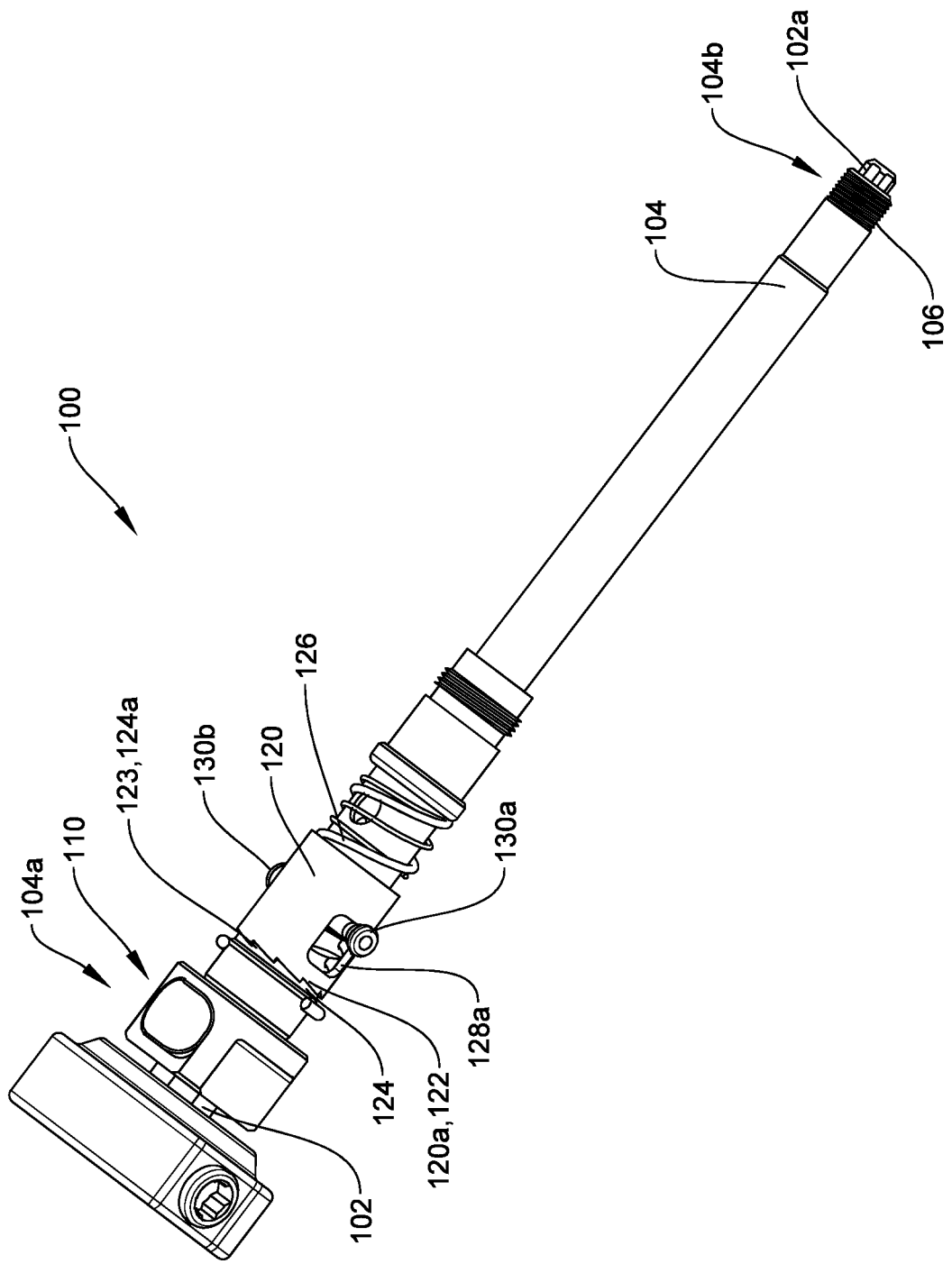
FIG. 2 is a perspective view of the screw inserter instrument of FIG. 1A, with the locking sleeve removed.
Figure 3:
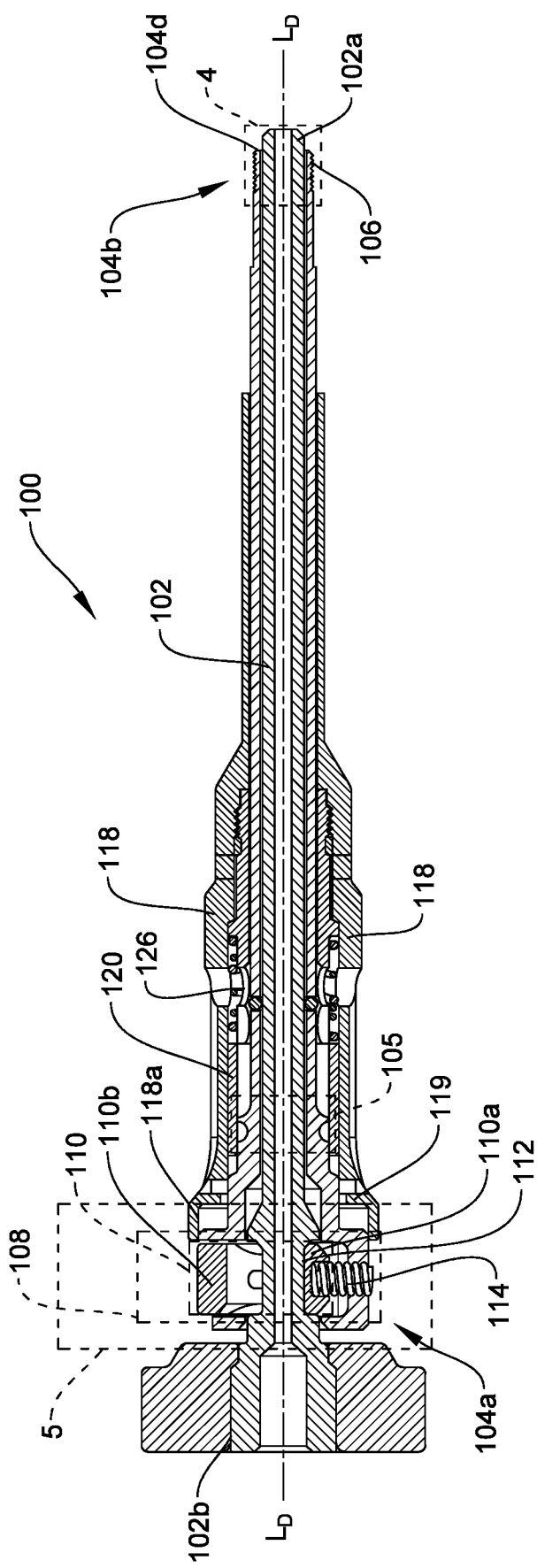
FIG. 3 is a cross-sectional view of the screw inserter instrument of FIG. 1A taken at 3-3.
Figure 4:
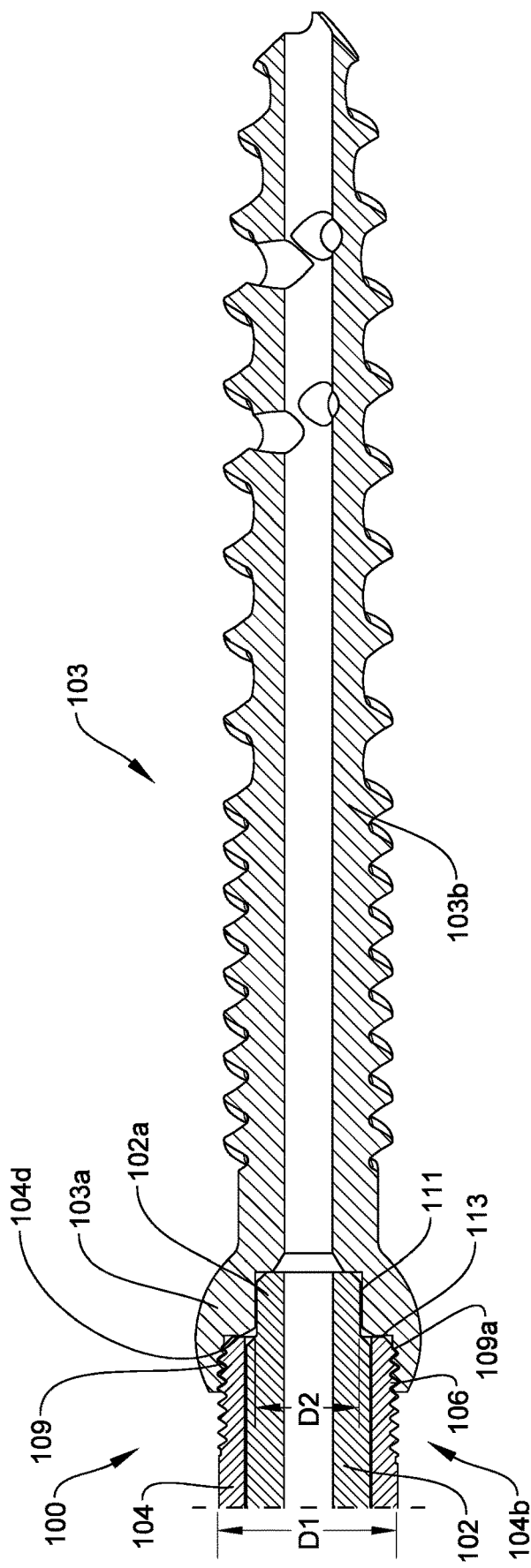
FIG. 4 is a magnified cross-sectional view of a portion of the screw inserter instrument of FIG. 3 taken at 4, showing the retaining sleeve coupled to an exemplary bone screw.

While the driver shaft 102 can have a variety of configurations, the driver shaft 102, as shown in FIGS. 1A-3, 6A, and 7A, has a generally elongate configuration with a distal tip 102a that is configured to couple to a bone screw, such as bone screw 103 in FIG. 4. Further, a proximal end of 102b the driver shaft 102 can be coupled to a first handle (not shown), also referred to herein as a proximal handle, such that rotation of the first handle in a first direction (e.g., clockwise) can cause concurrent rotation of the driver shaft 102 effective to drive the coupled bone screw into bone. The first handle and the driver shaft 102 are collectively referred to herein as a screw drive assembly.

The bone screw can include a proximal head portion with proximal and distal cavities defined therein. The proximal cavity can be substantially cylindrical with an internal thread formed therein for engaging a corresponding threaded portion of the retaining sleeve 104, as discussed below. The distal cavity can be shaped to non-rotatably engage the bone screw with the distal tip 102a of the driver shaft 102. As such, the distal tip 102a of the driver shaft 102 can have a variety of shapes and sizes, which depend at least in part on the shape and size of the distal cavity of the bone screw. As shown in FIGS. 1A-3, in this illustrated embodiment, the distal tip 102a of the driver shaft 102 has a hexagonal configuration. In other embodiments, the distal tip 102a can have any other suitable shape. As will be appreciated by a person skilled in the art, any bone screw, configured to engage bone can be used in conjunction with a screw inserter instrument including any of the screw inserter instruments described herein. Exemplary embodiments of bone screws are described in more detail in U.S. Patent Publication Nos. 2018/0014858 and 2018/0014862, each of which is hereby incorporated by reference in its entirety.

As shown in FIGS. 1A-3, 6A, and 7A, the retaining sleeve 104 extends from a proximal end 104a to a distal end 104b. The distal end 104b of the retaining sleeve 104 is configured to couple with a bone screw, like bone screw 103 in FIG. 4. While the distal end 104b of the retaining sleeve 104 can have a variety of configurations, the distal end 104b, as shown, includes threads 106 that are configured to threadably engage with corresponding internal threads of the proximal cavity of a bone screw (not shown). In this illustrated embodiment, the retaining sleeve 104 is disposed around a portion of the driver shaft 102 such that the retaining sleeve 104 extends between the proximal end 102b and distal tip 102a of the driver shaft 102. In this way, the distal tip 102a of the driver shaft 102 is exposed such that it can ultimately engage with a bone screw, like bone screw 103 in FIG. 4, as discussed below. As such, a bone screw can be coupled to the screw inserter instrument 100, for example, by inserting the distal tip 102a into a distal cavity of the bone screw and threadably engaging the distal end 104b of the retaining sleeve 104 to the proximal cavity of the bone screw.

FIG. 4 illustrates an exemplary bone screw 103 coupled to the screw inserter instrument 100. The bone screw 103 is cannulated and includes a head portion 103a and a threaded shaft 103b extending distally therefrom. The head portion 103a includes a threaded proximal cavity 109 and a non-threaded distal cavity 111, each of which are defined therein. As shown, the distal tip 102a of the driver shaft 102 is positioned within and non-rotatably engaged with the distal cavity 111, and a portion of the threads 106 of the retaining sleeve 104 are threadably engaged with corresponding internal threads 109a of the proximal cavity 109. In this illustrated embodiment, the proximal cavity 109 has a diameter (D1) that is larger than a diameter (D2) of the distal cavity 111, thereby creating a shoulder 113 within the head portion 103a of the bone screw 103. As a result, the distal end 104b of the retaining sleeve 104 is threaded into the proximal cavity 109 until the distal-most end 104d of the retaining sleeve 104 comes into contact with the shoulder 113.

Figure 5:
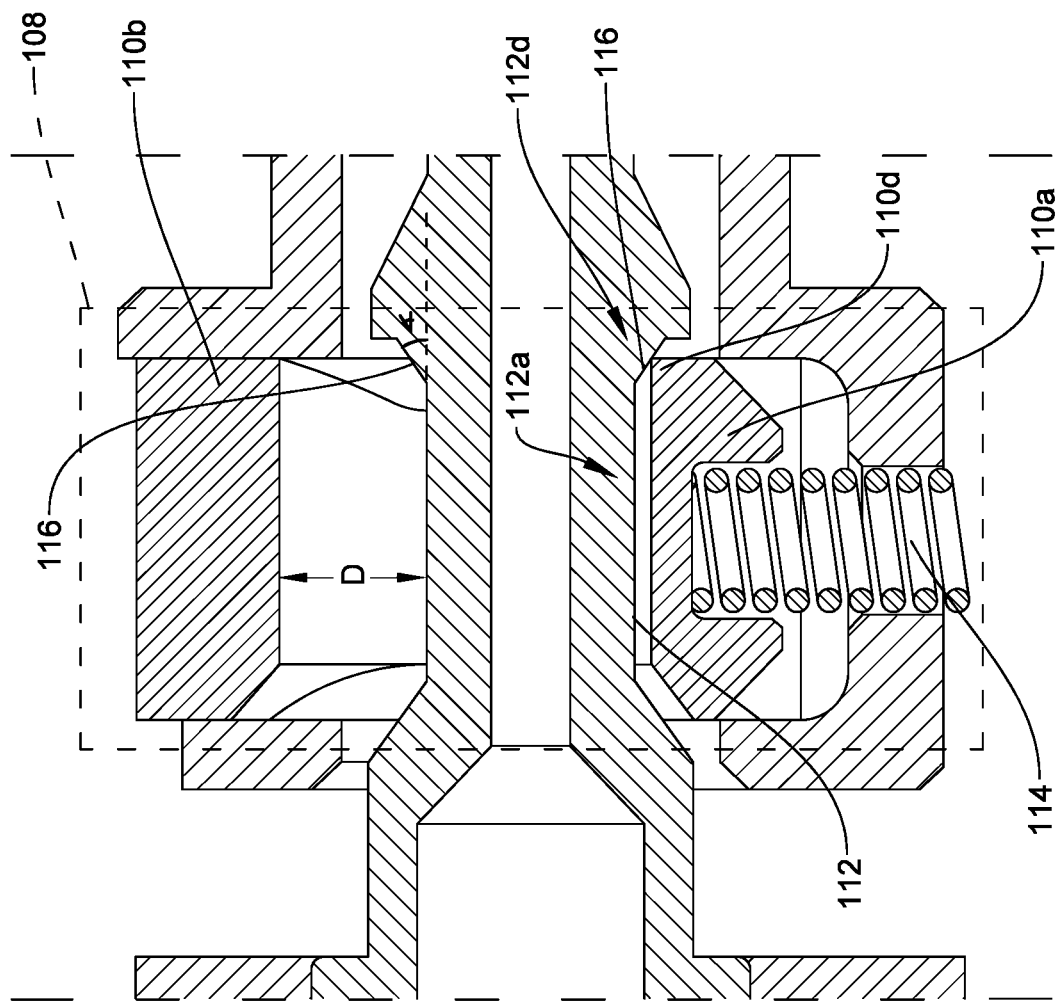
FIG. 5 is a magnified cross-sectional view of a portion of the screw inserter instrument of FIG. 3 taken at 5.

The proximal end 104a of the retaining sleeve 104 can be selectively coupled to the driver shaft 102 through a coupling mechanism 108. The coupling mechanism 108 can have a variety of configurations. For example, the coupling mechanism 108, as shown in FIG. 3 and in more detail in FIG. 5, includes a release button 110 that engages with a groove 112 of the driver shaft 102 adjacent to the proximal end 102b of the driver shaft 102. In particular, the release button 110 includes a first portion 110a that is configured to engage the groove 112, and a second portion 110b that is configured to be spaced from the groove 112 at a distance (D). This distance, as described in more detail below, can allow the second portion 110b to be selectively depressed towards the groove 112 so as to move the first portion 110a away from the groove 112, thereby decoupling the retaining sleeve 104 and the driver shaft 102. As shown in FIGS. 3 and 5, the release button 110 is engaged to the driver shaft 102 via a biasing element 114 in an extended configuration. While the biasing element 114 can have a variety of configurations, the biasing element 114, as shown in FIGS. 3 and 5, is in the form of a helical spring that biases the first portion 110a of the release button 110 toward the groove 112 and the second portion 110b of the release button 110 away from the groove 112 at distance (D).

In use, the driver shaft 102 is inserted into the retaining sleeve 104 until the first portion 110a of the release button 110 slides into contact with and engages the groove 112 of the driver shaft 102. To remove the driver shaft 102 from the retaining sleeve 104, the release button 110 can be actuated to cause the first portion 110a of the release button 110 to move away from, and thus disengage, the groove 112. For example, a user can actuate the release button 110 by applying sufficient force to the second portion 110b thereof such that the second portion 110b moves towards the groove 112. This causes the first portion 110a of the release button 110 to shift away from the groove 112 and the biasing element 114 to move into a compressed configuration. As a result, the first portion 110a of the release button 110 disengages the groove 112 of the driver shaft 102, thereby allowing the driver shaft 102 to be slidably removed. In other embodiments, other coupling mechanisms can be used.

Further, the groove 112 of the driver shaft 102 can include additional features that are configured to engage with the retaining sleeve 104. For example, as shown FIG. 5, a distal portion 112d of the groove 112 includes an angled interface 116 that can be used to bias the driver shaft 102 in a distal direction. The angled interface 116 can extend at various angles relative to an intermediate portion 112a of the groove 112. In the illustrated embodiment, the angled interface extends at a transverse angle (4) that is greater than 0 degrees and less than 90 degrees relative to the intermediate portion 112a of the groove 112. In other embodiments, the angle can be about 35° to 45°. In one embodiment, the angle can be about 45°.

In use, once the retaining sleeve 104 is coupled to a bone screw, a distal end 110d of the release button 110 engages the angled interface 116, causing the distal end 110d of the release button 110 and groove 112 to be in direct contact. This direct contact biases the driver shaft 102 in a distal direction. Further, this engagement removes any clearance between the distal end 110d of the release button 110 and the angled interface 116 of the groove 112. As a result, this engagement, along with having the distal-most end of the retaining sleeve 104 bottoming out on a shoulder within the bone screw, as discussed above, can inhibit toggling of the bone screw relative to the driver shaft 102 during screw insertion. Further, by only having a portion of the release button 110 engage directly with the angled interface 116, the release button 110 can be easily actuated without requiring disengagement (e.g., unthreading) of the retaining sleeve 104 from the bone screw due to the retaining sleeve 104 engagement with the shoulder of the bone screw and the clearance that remains between other portions of the release button 110 and the groove 112. As such, the retaining sleeve 104 can remain threadably engaged with the bone screw while the driver shaft 102 is disengaged via the release button 110, and thus removed therefrom. Once the driver shaft 102 is removed from the bone screw, other components can be inserted through the retaining sleeve 104 and into the coupled bone screw to carry out additional procedures, such as those described in U.S. Pat. No. 9,265,548 and in U.S. patent application Ser. No. 16/439,977, filed on Jun. 13, 2019, entitled "Instruments and Methods for Delivering Bone Cement to a Bone Screw," each of which is incorporated by reference herein in its entirety.

Figures 7A, 7B:
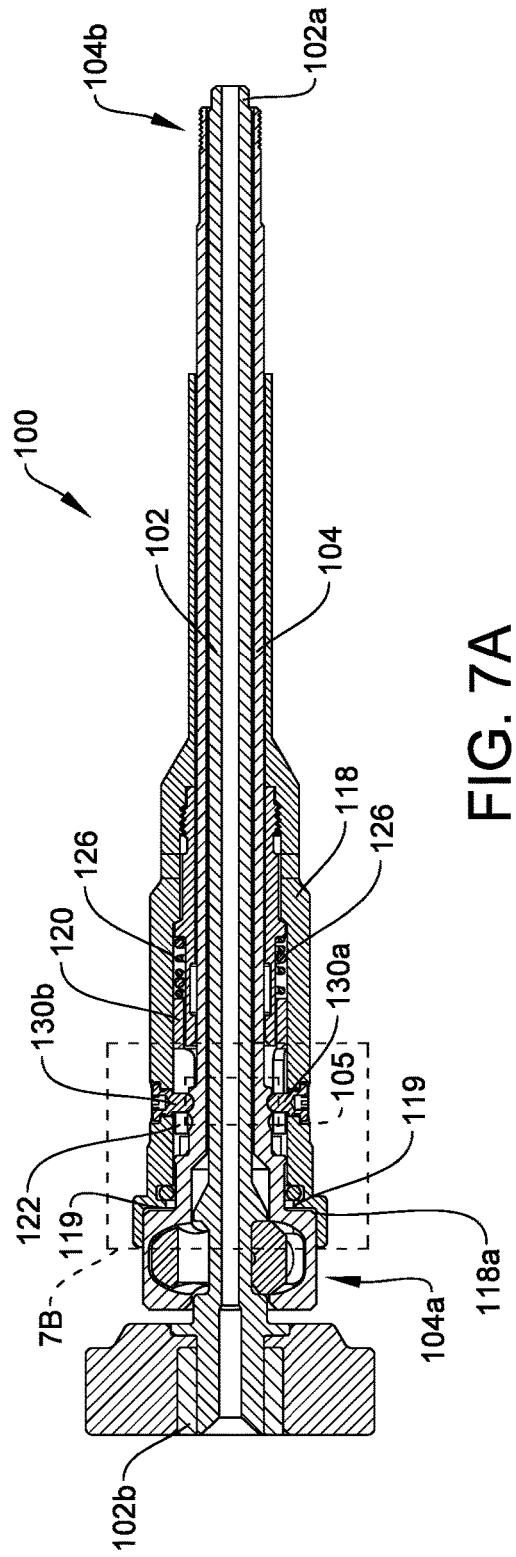
FIG. 7A is a cross-sectional view of the screw inserter instrument of FIG. 6A, showing the locking sleeve in a second or engaged position.
FIG. 7B is a magnified cross-sectional view of a portion of the screw inserter instrument of FIG. 7A taken at 7B.

As further shown in FIGS. 1A, 3, and 6A-7B, the locking sleeve 118 is disposed around a portion of the retaining sleeve 104. The locking sleeve 118 is configured to translate (e.g., by user activation) between a first or disengaged position (FIGS. 1A and 6A-6B) and a second or engaged position (FIGS. 7A and 7B). As discussed in more detail below, when the locking sleeve 118 is in its first or disengaged position, the driver shaft 102 and the retaining sleeve 104 can be rotated while the locking sleeve 118 remains stationary. As a result, the driver shaft 102 and the retaining sleeve 104 can be rotated together as a unit in a first direction (e.g., clockwise) to drive a bone screw into bone while simultaneously rotating the retaining sleeve 104 so that it remains engaged with the bone screw. When the locking sleeve 118 is in the second or engaged position, the retaining sleeve 104 and the locking sleeve 118 can be rotated while the driver shaft 102 remains stationary. As a result, the retaining sleeve 104 the locking sleeve 118 can rotate together as a unit in a second direction that is opposite the first direction (e.g., counterclockwise) to allow the retaining sleeve 104 to disengage from the implanted bone screw, while the driver shaft 102 remains stationary so that it does not cause translation of the implanted bone screw relative to bone. Thus, the locking sleeve 118 allows the retaining sleeve 104 to remain coupled to the bone screw during implantation and allows disengagement of the retaining sleeve 104 from the bone screw after implantation.

Figure 1B:
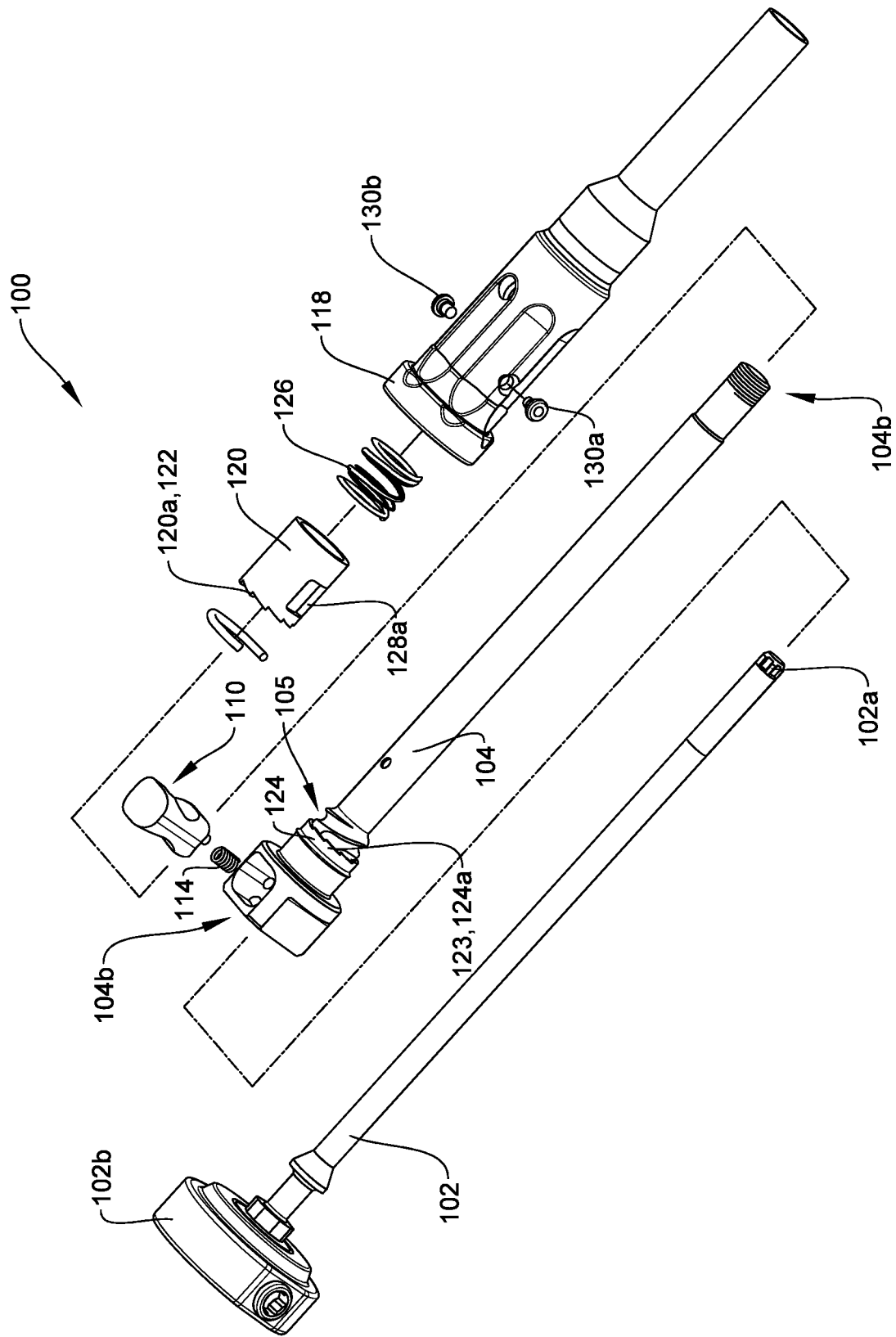
FIG. 1B is a partial exploded view of the screw inserter instrument of FIG. 1A.

The locking sleeve 118 is coupled to the retaining sleeve 104 by a coupling element 120, as shown in FIGS. 2-3 and 6A-7B. The coupling element 120, which is shown in more detail in FIGS. 1B and 2, is disposed between the retaining sleeve 104 and the locking sleeve 118. While the coupling element 120 can have a variety of configurations, as shown in FIGS. 2-3 and 6A-7B, the coupling element 120 is in the form of a first cylindrical collar having a first set of teeth 122 at a first end 120a. As shown, the first set of teeth 122 engage with a second set of teeth 123 at a first end 124a of a second cylindrical collar 124 that is disposed around the retaining sleeve 104.

While the first and second sets of teeth 122, 123 can have a variety of configurations, as shown in FIGS. 1B and 2, the first set of teeth 122 extend at a first angular orientation and the second set of teeth 123 extend at a complementary second angular orientation. Once the driver shaft 102 and retaining sleeve 104 are coupled to the bone screw, and therefore rotatably coupled to each other, the engagement of the first and second sets of teeth 122, 123 allows the driver shaft 102 and the retaining sleeve 104 to rotate together in the first direction (e.g., clockwise) to drive the bone screw into bone while the locking sleeve 118 is held stationary. In this way, during screw insertion, the retaining sleeve 104 will not remain stationary relative to the bone screw, which would result in unthreading of the retaining sleeve 104 from the bone screw. Instead, the retaining sleeve 104 rotates with and thus remains coupled to the bone screw as it is driven into bone.

As further shown in FIGS. 3, 6A, and 7A, a biasing element 126 resides within the locking sleeve 118. While the biasing element 126 can have a variety of configurations, the biasing element 126, in this illustrated embodiment, is a helical spring. The biasing element 126 can continuously bias the first set of teeth 122 toward the second set of teeth 123. As a result, the first and second sets of teeth 122, 123 remain engaged independent of the position of the locking sleeve 118. Further, as discussed below, the biasing element 126 can bias the locking sleeve 118 distally, thereby biasing the locking sleeve 118 to its first or disengaged position.

Further, as shown in FIGS. 1B, 2, 6B, and 7B, the coupling element 120 includes first and second cutout portions 128a, 128b defined therein and positioned proximate to the first end 120a thereof. While the first and second cutout portions 128a, 128b can have a variety of shapes and sizes, each cutout portion 128a, 128b, as shown in FIGS. 1B and 2, is substantially rectangular in shape. The first and second cutout portions 128a, 128b are sized and shaped to allow first and second locking pins 130a, 130b, which extend radially inward from the locking sleeve 118, to extend therethrough for selective engagement with a threaded portion 105 of the retaining sleeve 104, as discussed in more detail below. Further, the size of the first and second cutout portions 128a, 128b can be designed to allow relative movement between the locking sleeve 118 and the retaining sleeve 104 and to allow the locking sleeve 118 to return to the first position. Thus, the first and second cutout portions 128a, 128b can allow a certain amount of slippage between the locking sleeve 118 and the retaining sleeve 104.

When a bone screw is implanted, the retaining sleeve 104 can be disengaged from the implanted bone screw. This disengagement can be effected by movement of the locking sleeve 118 from its first or disengaged position to its second or engaged position. As will be described in more detail below, the locking sleeve 118 can be configured to move proximally and rotate in the second direction (e.g., counterclockwise) while the driver shaft 102 is held stationary, thus allowing the retaining sleeve 104 to disengage from the implanted bone screw. Thus, when the driver shaft 102 is held stationary and the locking sleeve 118 is moved to its second or engaged position, further rotation of the locking sleeve 118 in the second direction will cause concurrent rotation of the retaining sleeve 104. As a result, this will unthread the retaining sleeve 104 from the implanted bone screw.

For example, in use, the locking sleeve 118 can transition from the first/disengaged position (FIGS. 1A, 3, and 6A-6B) toward the second/engaged position (FIGS. 7A and 7B) by moving (pulling) the locking sleeve 118 in a proximal direction (e.g., towards a first handle coupled to the proximal end 102b of the driver shaft 102). In this way, the pulling force applied by a user can overcome the biasing force of the biasing element 126, and consequently, move the biasing element 126 from its expanded configuration to a compressed configuration. This allows the locking sleeve 118 to move in a proximal direction relative to the retaining sleeve 104. The axial translation of the locking sleeve 118 in the proximal direction causes axially translation of locking pins 130a, 130b that extend radially inward from the locking sleeve 118. This axial translation causes the locking pins 130a, 130b to abut an end 105a of a threaded portion 105 of the retaining sleeve 104. With the locking sleeve 118 pulled proximally, the locking sleeve 118 can be rotated in the second direction (e.g., counterclockwise) relative to the retaining sleeve 104 to cause the locking pins 130a, 130b to threadably engage and proximally and rotatably translate through a portion of the threaded portion 105 of the retaining sleeve 104 (e.g., towards the first handle). As illustrated in FIGS. 7A-7B, the locking sleeve 118 has been rotated 35 degrees counterclockwise. In other embodiments, the locking sleeve 118 can be rotated in the second direction from about 0° to 180° relative to the retaining sleeve 104. A person skilled in the art will appreciate that the amount of rotation of the locking sleeve is dependent at least upon the thread pitch and the spatial clearance between the locking sleeve and other parts of the instrument 100.

As the locking sleeve 118 is rotated, the locking pins 130a, 130b ultimately reach a proximal position within the cut-out portions 128a, 128b in which a flange 119 extending from an inner surface 118a of the locking sleeve 118 comes into contact with the proximal end 104a of the retaining sleeve 104, as shown in FIGS. 7A and 7B. This causes the locking sleeve 118 to move into its second/engaged position. In particular, the proximal end 104a prevents the locking sleeve 118 from further proximal translation relative to the retaining sleeve 104. This causes the locking sleeve 118 to bottom out and the locking pins 130a, 130b to be retained within, and thus prevented from moving distally through, the threaded portion 105 of the retaining sleeve 104. As a result, when the locking sleeve 118 is in the second/engaged position, further rotation of the locking sleeve 118 in the second direction (counterclockwise) causes concurrent rotation of the retaining sleeve 104 in the same direction relative to the driver shaft 102, which is held stationary to maintain the implanted bone screw in a fixed position. This rotation of the locking sleeve 118 and the retaining sleeve 104 in the second direction causes the distal end 104b of the retaining sleeve 104 to threadably disengage from the implanted bone screw.

Once the retaining sleeve 104 and the driver shaft 102 are removed from the implanted bone screw, the locking sleeve 118 can return to its first position. For example, in use, when the locking sleeve 118 is in its second position, a user can release the locking sleeve 118. This causes the biasing element 126 to expand from its compressed configuration back towards its expanded configuration, thereby moving the locking sleeve 118 toward its first/engaged position. In this way, as the biasing element 126 forces the locking sleeve 118 in a distal direction, the locking pins 130a, 130b distally translate past the end 105a of the threaded portion 105 of the retaining sleeve 104.

As previously mentioned, the screw inserter instruments can be used to implant a bone screw assembly into bone. Any suitable method can be used for operating any of the screw inserter instruments having a sleeve assembly as described herein. For example, when operating the screw inserter instrument 100 (FIGS. 1A-7B), the retaining sleeve 104 can be rotated relative to the driver shaft 102, with the driver shaft 102 held stationary, to threadably engage the retaining sleeve 104 with a bone screw coupled to the distal tip 102a of the driver shaft 102. Once coupled to the bone screw, a handle on the driver shaft 102 can be rotated in a first direction while the locking sleeve 118 is held stationary to drive the bone screw into bone. This rotation can also cause the retaining sleeve 104 to rotate with the driver shaft 102, as explained above. Once the bone screw is implanted in bone, the locking sleeve 118 can be moved from the first position to the second positon relative to the retaining sleeve 104. This can be achieved by pulling the locking sleeve 118 proximally and by rotating the locking sleeve 118 counterclockwise relative to the retaining sleeve 104. The driver shaft 102 can be held stationary while the locking sleeve 118 is rotated into the locked position. When in the second position, rotation of the locking sleeve 118 counterclockwise while holding the driver shaft 102 stationary can cause the retaining sleeve 104 to rotate and thereby threadably disengaging the retaining sleeve from the bone screw, as explained above.

The locking sleeve described herein, therefore, provides a location for a user to grasp the screw inserter instrument such that the driver shaft can be rotated to drive a bone screw coupled thereto into bone. This grasping location also allows the retaining sleeve to be rotated with the driver shaft in the same direction, and as a result, prevents detachment of the retaining sleeve from the coupled bone screw during bone screw insertion. Further, the locking sleeve provides a location for a user to grasp the screw inserter instrument and rotate the locking sleeve while holding the driver shaft to allow the retaining sleeve to be detached from the implanted bone screw.

In some embodiments, a screw inserter instrument can also include a stop sleeve that is configured to limit an insertion depth of a bone screw being driven into bone. The stop sleeve can be partially disposed around the retaining sleeve such that a portion of the stop sleeve can surround at least a portion of the bone screw coupled to the retaining sleeve. The length of overlap can be associated with the length of bone screw needed for polyaxial head assembly. As such, the stop sleeve can be configured to limit insertion of a portion of the bone screw into bone. For example, the stop sleeve can provide tactile and visual feedback to the user when the bone screw has reached a desired insertion depth. Further, in certain embodiments, the stop sleeve can be coupled to the retaining sleeve to allow the retaining sleeve and the stop sleeve to rotate together, whereas in other embodiments, the stop sleeve can freely rotate relative to the retaining sleeve.

FIGS. 8A-8B illustrate an embodiment of a screw inserter instrument 200 having a stop sleeve 232. Aside from the differences described in detail below, the screw inserter instrument 200 can be similar to the screw inserter instrument 100 (FIGS. 1A-7B) and is therefore not described in detail herein. Further, for purposes of simplicity, certain components of the screw inserter instrument 200 are not illustrated in FIGS. 8A-8B. Further, for illustration purposes only, a bone screw 234 is coupled to the screw inserter instrument 200.

The stop sleeve 232 can have a variety of configurations. For example, the stop sleeve 232 shown in FIGS. 8A-8B includes an elongated cylindrical body 236 disposed around a portion of the retaining sleeve 204 and having a head 238 extending distally therefrom at a length ($L_H$). The elongated cylindrical body 236 and the head 238 include windows 239a, 239b defined therein on opposed sides thereof. The windows 239a, 239b, for example, can allow a user to view the bone screw 234 as it is being coupled to the retaining sleeve 204. Further, a proximal end 232p of the stop sleeve 232 can be fixedly coupled to a distal end 218d of the locking sleeve 218. As a result, movement of the locking sleeve 218 effects concurrent movement of the stop sleeve 232. A person skilled in the art will appreciate that in other embodiments the proximal end 232p of the stop sleeve 232 can be coupled to the distal end 218d of the locking sleeve 218 in such a way that allows the stop sleeve 232 to freely rotate relative to the locking sleeve 218, and consequently, relative to the retaining sleeve 204 and driver shaft 202.

As further shown, a portion 238a of the head 238 overlaps with a portion of the bone screw 234 when the bone screw 234 is fully engaged with the retaining sleeve 204. As a result, during use, as the bone screw 234 is driven into bone, a distal end 238d of the head 238 will eventually come into contact with a surface of the bone. This contact will indicate to the user (e.g., by tactile and visual feedback) that the bone screw 234 has reached a predetermined insertion depth. As noted above, the length of the overlap can be predetermined to provide an amount of clearance effective to allow attachment of a polyaxial head assembly (not shown) to the bone screw 234.

While the head 238 can have a variety of configurations, the head 238 in FIGS. 8A-8B has a substantially conical shaped configuration. In this illustrated embodiment, the head 238 has a first outer diameter that increases distally along a first portion 240a, a second outer diameter that is substantially constant along a second portion 240b, and a third outer diameter that decreases distally along a third portion 240c. A person skilled in the art will appreciate that in other embodiments the head 238 can have an outer diameter that increases or decreases distally or remains constant along the entire length La of the head 238. Further, in other embodiments, the head 238 can have other suitable shapes and sizes.

FIGS. 9A-9B illustrate another embodiment of a stop sleeve 332 coupled to a screw inserter instrument 300. Aside from the differences described in detail below, the screw inserter instrument 300 can be similar to screw inserter instrument 100 (FIGS. 1A-7B) and is therefore not described in detail herein. Further, for purposes of simplicity, certain components of the screw inserter instrument 300 are not illustrated in FIGS. 9A-9B. Further, for illustration purposes only, a bone screw 334 is coupled to the screw inserter instrument 300.

The stop sleeve 332 shown in FIGS. 9A-9B includes an elongated body 336 disposed around a portion of the retaining sleeve 304 and having a head 338 extending distally therefrom at a length ($L_H$). As shown, a portion 338a of the head 338 overlaps with a portion of the bone screw 234. In this illustrated embodiment, the head 338 has a substantially u-shaped configuration with a base 343a and two opposing legs 343b, 343c extending therefrom. Further, the head includes windows 340a, 340b, and 340c positioned therearound.

As further shown in FIGS. 9A-9B, a proximal end 332p of the stop sleeve 332 is coupled to a distal end 318d of the locking sleeve 318 through a coupling element 339. While the coupling element 339 can have variety of configurations, in this illustrated embodiment, the coupling element 339 is in the form of a generally cylindrical body that extends from a first end 339a to a second end 339b. The coupling element 339 includes an annular ring 337 that extends radially outward therefrom. As shown, the annular ring 337 engages an internal groove 319 defined within the locking sleeve 318 such that the first end 339a of the coupling element 339 resides within the locking sleeve 318. As shown, the second end 339b of the coupling element 339 is positioned within a cavity 341 defined within the proximal end 332p of the stop sleeve 332. Further, a first set of threads 342a at the second end 339b of the coupling element 339 is engaged with a second set of threads 342b of the cavity 341 in the stop sleeve 332. As a result, the stop sleeve 332 can be mated to the locking sleeve 318 in such a manner that allows the stop sleeve 332 to freely rotate relative the locking sleeve 318, and consequently, relative to the retaining sleeve 304 and driver shaft 302.

In certain embodiments, the stop sleeve can be formed of, or coated with, an insulating material that is configured to electrically insulate the retaining sleeve and/or driver shaft during neuromonitoring. For example, the stop sleeve can be formed of one or more plastics that act as a barrier such that current being applied to the retaining sleeve and/or driver shaft would be isolated from surrounding tissue at the surgical site. Additionally or alternatively, a radiopaque material can be inserted into a distal end of the stop sleeve to allow a user to visualize the interface between the stop sleeve and the bone screw before applying a current.

In some embodiments, a screw inserter instrument can include a stylet assembly, like stylet assembly 450 in FIGS. 10A-10B, for controlling the positioning of a stylet relative to a bone screw that is coupled to a distal end of the instrument, like instrument 100 in FIGS. 1A-7B. In general, the stylet assembly can include a second handle, like second handle 450a in FIGS. 10A-10B, also referred to herein as a distal handle, and a stylet, like stylet 450b in FIGS. 10A-10B, that extends through a driver shaft, like driver shaft 402 in FIGS. 10A-10B, of the instrument. The axial position of the stylet can be adjusted through rotation of the second handle. To prevent the coupled bone screw from being inserted or removed from bone during the advancement and retraction of the stylet, a user can apply counter torque to the first handle of the instrument during the rotation of the second handle. Thus, as discussed in more detail below, a user can rotate the second handle, while holding the first handle stationary, to can cause axial translation of the stylet. Conversely, during use, once the stylet is positioned relative to bone, the second handle is held stationary while the first handle is rotated to drive the bone screw into bone. During advancement of the screw, it may be desirable to allow a user to continuously rotate the driver shaft of the instrument without the need to remove his/her hand from the first handle. Thus, a clutch mechanism with a ratcheting feature can be provided, as well as a switch mechanism. The switch can allow a user to switch the first handle between a first mode, e.g., a locked configuration, in which the first handle can be held stationary to apply a counter torque during rotation of the second handle, and a second mode, e.g., an unlocked configuration, in which the ratcheting feature is activated. The ratcheting feature allows the first handle to continuously drive the driver shaft in only one direction while preventing motion in the opposite direction to thereby drive the bone screw into bone. This configuration allows a user to maintain contact with the first handle and to advance the screw into bone more rapidly.

FIGS. 10A-10B illustrate an exemplary screw inserter instrument 400. Aside from the differences described in detail below, the screw inserter instrument 400 can be similar to screw inserter instrument 100 (FIGS. 1A-7B) and is therefore not described in detail herein. For purposes of simplicity, certain components of the screw inserter instrument 400 are not illustrated in FIGS. 10A-10B. The screw inserter instrument 400 generally includes a first handle 446, a driver shaft 402, a driving tube 448, and stylet assembly 450. The first handle 446 and the driver shaft 402 are collectively referred to herein as a screw drive assembly. While the screw inserter instrument 400 also includes a retaining sleeve 404, a locking sleeve 418, and a stop sleeve 432, which are similar to those described above, a person skilled in the art will appreciate that in certain embodiments, the retaining sleeve 404 and/or the locking sleeve 418, and/or the stop sleeve 432 can be omitted.

As shown in FIG. 10B, a proximal end 402p of the driver shaft 402 is coupled to a distal end 448d of the driving tube 448, and a proximal end 448p of the driving tube 448 is mated to the first or proximal handle 446. The driving tube 448 can be in the form of a generally elongated hollow tube with a proximal portion 448a and a distal portion 448b. While the first handle 446 can be selectively mated to the driving tube 448 using a variety of mechanisms, the proximal end 448p of the driving tube 448 includes a mating feature 449 formed thereon for mating with an inner surface 463b of a distal portion 463 of a coupling member 452 disposed within the first handle 446. In this illustrated embodiment, the mating feature 449 on the driving tube 448 is a male hex feature and, as shown FIGS. 11E-11G, the inner surface 463b of the distal portion 463 is the form of a female hex feature. In other embodiments, the mating features can have any other configuration that is suitable to selectively mate the first handle 446 to the driving tube 448.

The stylet assembly 450 includes a second handle 450a and a stylet 450b, as shown in FIGS. 10A-10B. The second handle 450a is rotatably positioned over the distal portion 448b of the driving tube 448, and the stylet 450b extends through driver shaft 402. In use, the first handle 446 is held stationary while the second handle 450a is rotated to distally advance or proximally retract the stylet 450b relative to the driver shaft 402. Further, to drive a bone screw that is coupled to the screw drive assembly into bone, the second handle 450a is held stationary while the first handle 446 and driver shaft 402 are rotated. The stylet assembly 450 can include a carrier 450c that is coupled to the stylet 450b and moveably disposed within the driving tube 448. Further details on the stylet assembly 450 and other exemplary stylet assemblies can be found in U.S. Patent Publication No. 2018/0368893 and in U.S. patent application Ser. No. 15/801,917, filed on Nov. 2, 2017, entitled "Bone Anchor Insertion Instruments and Methods," each of which is incorporated by reference herein in its entirety.

To prevent the driver shaft 402 from rotating during stylet advancement and retraction, the driver shaft 402 can be locked to the first handle 446 via a locking assembly 466, also referred to herein as a control mechanism, residing within the first handle 446. The locking assembly 466 can be configured to selectively lock the first handle 446 and driver shaft 402 to each other such that they rotate as a unit. As such, the locking assembly 466 has a locked configuration and an unlocked configuration. When the locking assembly 466 is in a locked configuration, a user can grasp and hold the first handle 446 stationary, and thus the driver shaft 402 stationary, while the second handle 450a is rotated to advance or retract the stylet 450b to a desired length. That is, the locking assembly 466 allows a user to apply a counter torque through the first handle 446 during rotation of the second handle 450a in either a clockwise or a counterclockwise direction, while also preventing the driver shaft 402 from rotating. As a result, during stylet advancement and retraction, axial translation of a bone screw (not shown) coupled to the distal tip 402a of the driver shaft 402 can be prevented. When the locking assembly 466 is in its unlocked configuration, the first handle 446 can couple to and rotate with the driver shaft 402 via a clutch assembly, like clutch assembly 480 in FIGS. 11H, which will be discussed in more detail below. The clutch assembly functions as a ratchet such that a user can continuously drive the driver shaft 402 in only one direction without removing their hand from the first handle 446.

The first handle 446 can have a variety of configurations that allow a user to effectively grasp the first handle 446 and operate the screw inserter instrument 400. For example, as shown in FIG. 10A, the first handle 446 can be in the form of a T-handle. The first handle 446 is shown in more detail in FIGS. 11A-11H, and includes a base member 454 and first and second arm members 456a, 456b extending outwardly therefrom in opposite directions. The first and second arm members 456a, 456b allow a user to easily grasp the first handle 446 for rotation thereof. Further, as shown in FIGS. 11D and 11E, the first and second arm members 456a, 456b each include a channel 457a, 457b extending therethrough along a longitudinal axis ($L_H$) of the first handle 446.

Figure 11C:
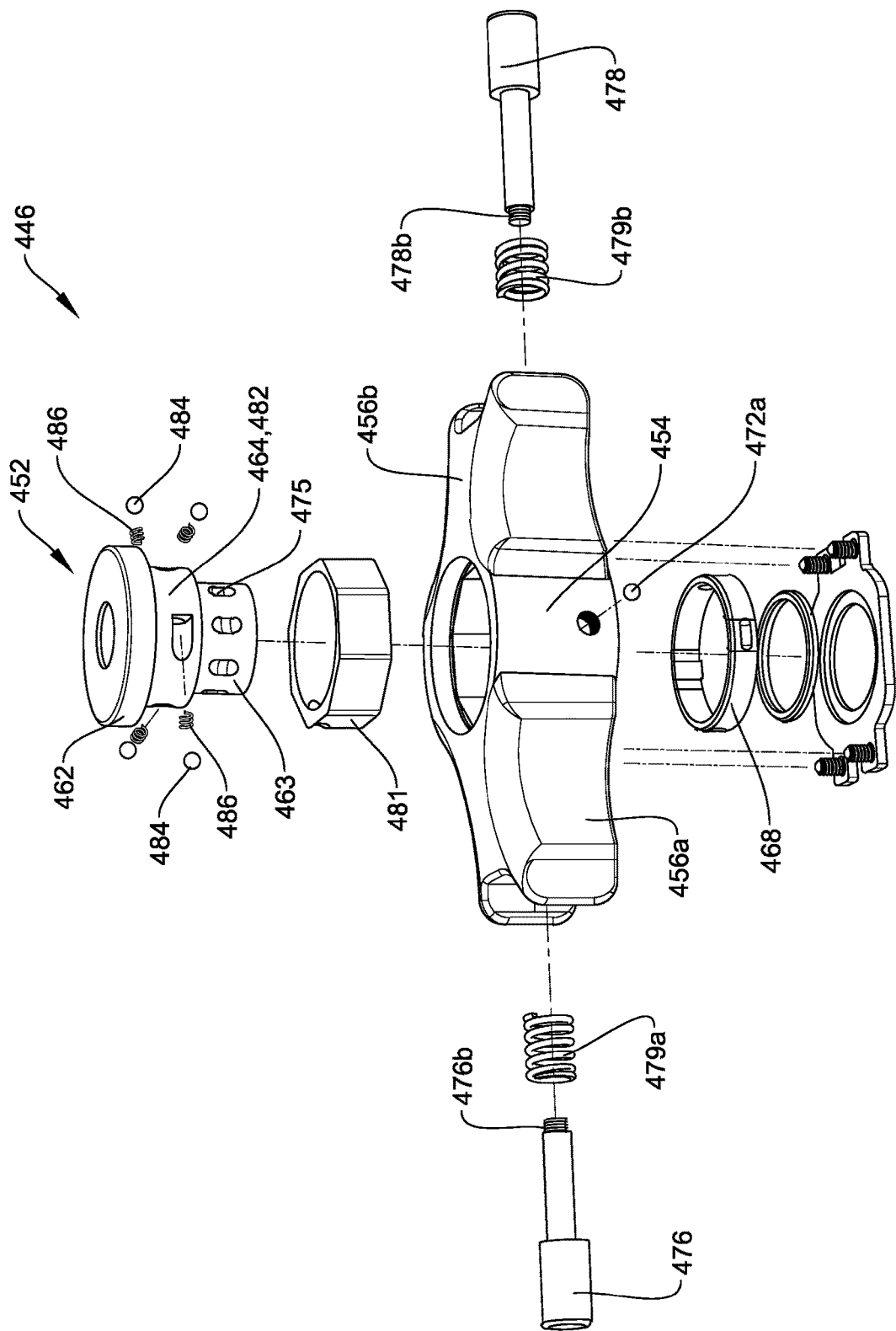
FIG. 11C is a partial exploded view of the first handle of FIG. 11A.

While the base member 454 can have a variety of configurations, as shown in FIGS. 11A-11G, the base member 454 includes a channel 454a that extends therethrough. As shown, the channel 454a extends along an axis that is transverse to the longitudinal axis ($L_H$) of the first handle 446. Further as shown in FIGS. 11D and 11E, a portion of the channel 454a is defined by an inner surface 459a of a first flange 459 that extends radially inward from an inner surface 454b of the base member 454. As a result, a first cavity 460 and a second cavity 461 in communication with the first cavity 460 via the channel 454a are formed within the base member 454.

Figure 11F:
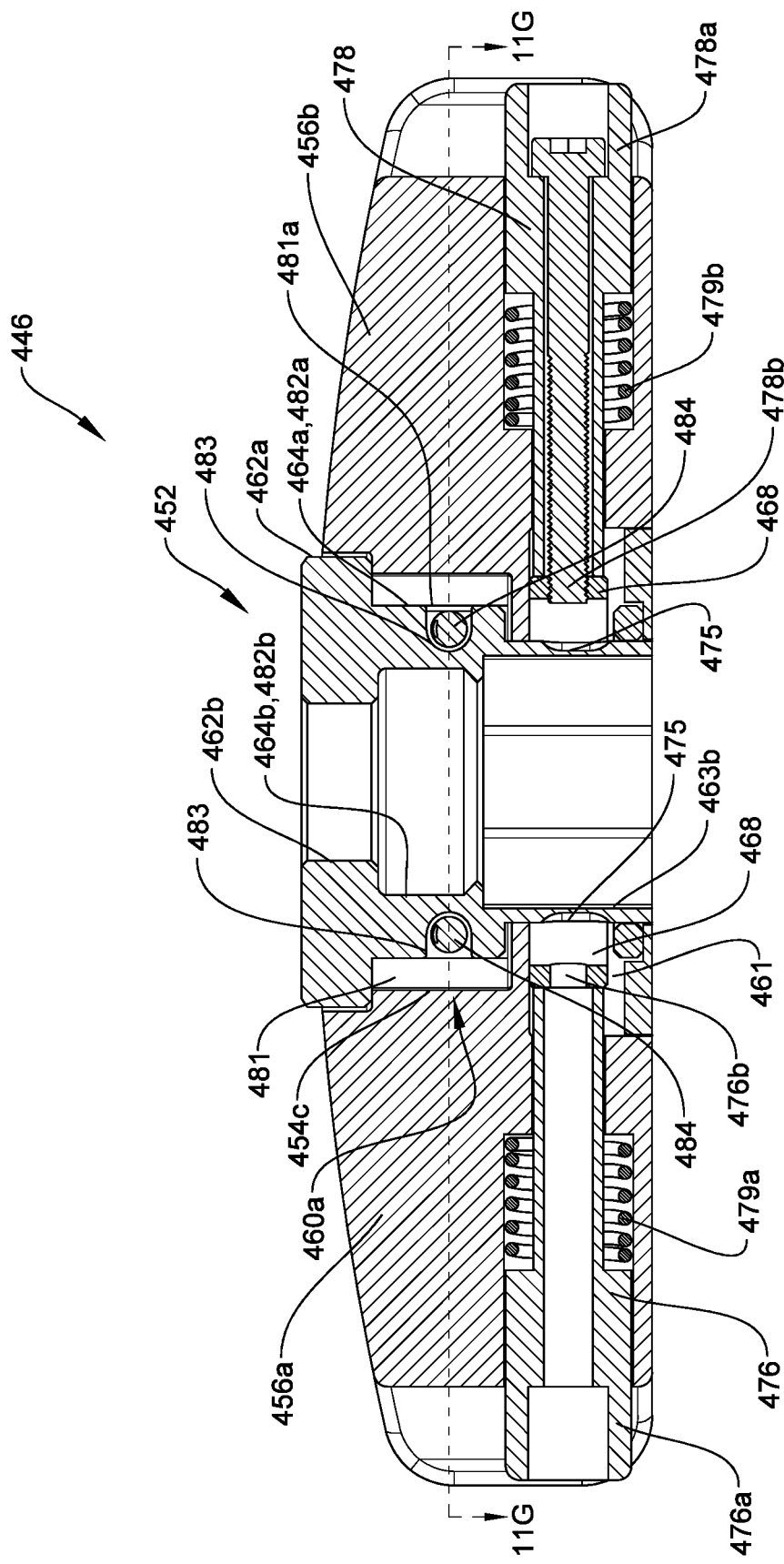
FIG. 11F is a cross-sectional view of the first handle of FIG. 11A taken at 11-11.

As further shown in FIGS. 11E and 11F, a coupling member 452 is positioned within and extends from the first cavity 460 into the second cavity 461 of the base member 454. The coupling member 452 can have a variety of configurations. In this illustrated embodiment, the coupling member 452 is in the form of a generally elongated hollow tube having a proximal portion 462, a distal portion 463, and in intermediate portion 464 extending therebetween. These portions 462, 463, 464 each have an outer surface 462a, 463a, 464a and an inner surface 462b, 463b, 464b in which each outer surface 462a, 463a, 464a is substantially circular in shape. As shown, the outer diameter of the coupling member 452 generally decreases distally along its length ($L_C$). In other embodiments, the coupling member 452 can have other suitable shapes and sizes. Further, the inner surface 463b of the distal portion 463 is substantially hexagonal in shape. As a result, this inner surface 463b functions as the female hex feature that is configured to receive a male hex feature on a driving tube 448 to mate the first handle 446 to the driving tube 448. The coupling member 452 includes additional features that form part of either a locking assembly 466 or a clutch assembly 480 that reside within the first handle 446, which will be discussed in more detail below.

Figure 11G:
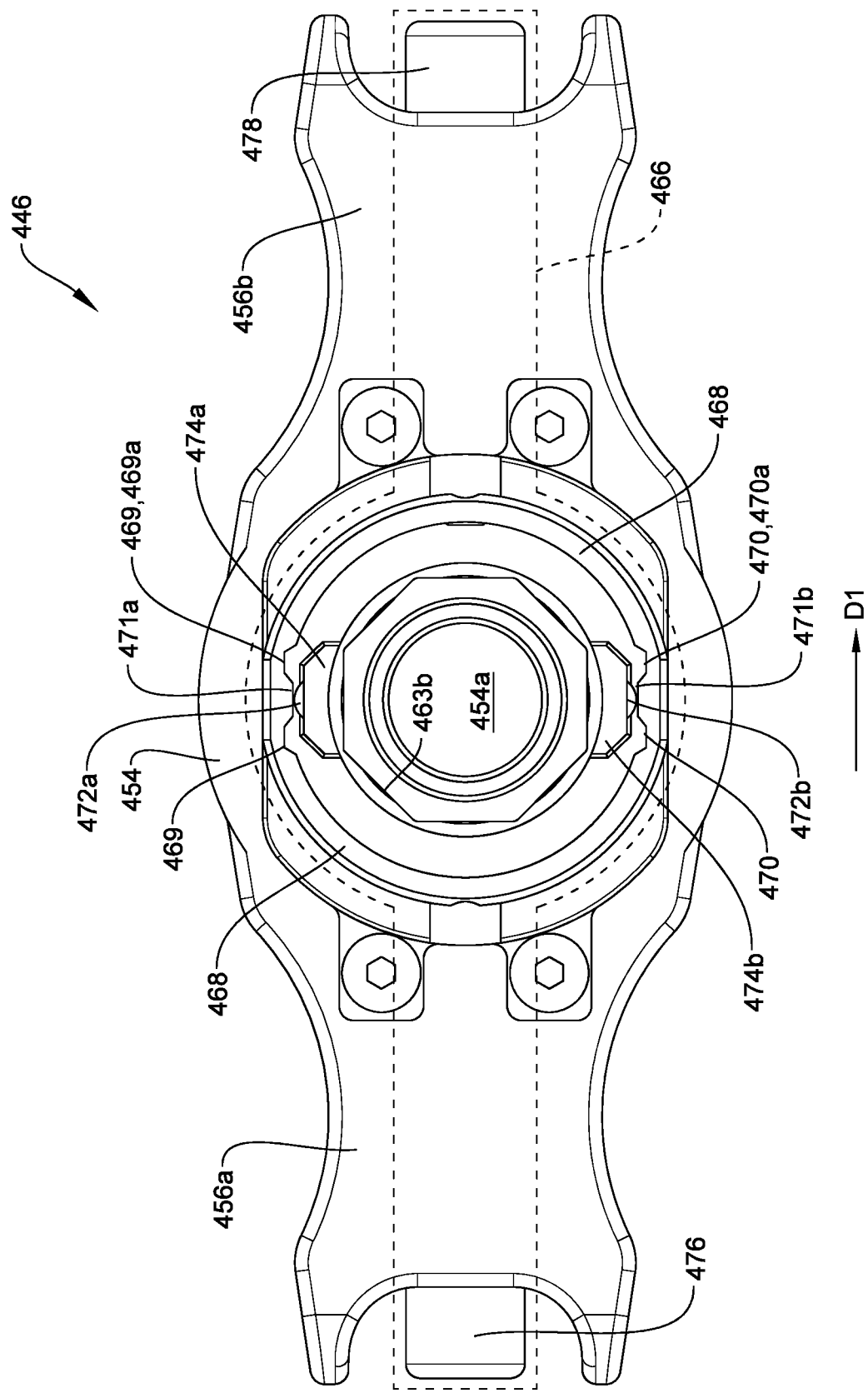
FIG. 11G is bottom view of the first handle of FIG. 11A, showing a locking assembly residing within the first handle.

The locking assembly 466 can have a variety of configurations. For example, as shown in FIGS. 11C, 11F, and 11G, the locking assembly 466 includes first and second trigger elements 476, 478 that are coupled to a locking ring 468 that is positioned within the second cavity 461 of the base member 454. In this illustrated embodiment, when the locking assembly 466 is in the locked configuration, the locking ring 468 is coupled to the driver shaft 402 such that the first handle 446 and driver shaft 402 are locked together and rotate as a unit. When the locking assembly 466 is in the unlocked configuration, the locking ring 468 is decoupled from the driver shaft 402, thereby allowing the driver shaft 402 to freely rotate relative to the first handle 446. As discussed in more detail below, the locking assembly 466 is biased to its locked configuration, and thus the first handle 446 and the driver shaft 402 are locked together until the locking assembly 466 is moved into its unlocked configuration.

While the first and second trigger elements 476, 478 can have variety of configurations, as shown in FIGS. 11F and 11G, each trigger element 476, 478 is generally in the form of an elongated cylindrical member having a first end 476a, 478a and a second end 476b, 478b. As shown, a portion of the first trigger element 476 extends through the channel 457a of the first arm member 456a and a portion of the second trigger element 478 extends through the channel 457b of the second arm member 456b. The first end 476a, 478a of each trigger element 476, 478 is therefore positioned outside of the first handle 446 and the second end 476b, 478b of each trigger element 476, 478 is fixedly coupled to the locking ring 468, as shown in FIGS. 11F and 11G. In other embodiments, the first handle 446 can include a trigger element(s) having other suitable configurations. For example, in one embodiment, at least one trigger element can take the form of a switch.

As shown in FIG. 11F, a first biasing element 479a is disposed within the channel 457a of the first arm member 456a and a second biasing element 479b is disposed within the channel 457b of the second arm member 456b. While the first and second biasing elements 479a, 479b can have a variety of configurations, each biasing element 479a, 479b, in this illustrated embodiment, is a helical spring. The first and second biasing elements 479a, 479b, when in the expanded configuration, can bias the first and second trigger elements 476, 478, respectively, in a first position, as shown in FIGS. 11F and 11G. As a result, the first and second trigger elements 476, 478 are biased to their first position, and consequently, the locking assembly 466 is biased to its locked configuration.

The locking ring 468 can have a variety of configurations. As shown in FIG. 11G, the locking ring 468 includes a first set of two adjacent recesses 469 defining a first engagement interface 471a therebetween and a second set of two adjacent recesses 470 defining a second engagement interface 471b therebetween. When the locking assembly 466 is in its locked configuration, the first and second engagement interfaces 471a, 471b frictionally engage with first and second engagement features 472a, 472b, respectively, as shown in FIG. 11G. While the engagement features 472a, 472b can have a variety of configurations, the engagement features 472a, 472b each have a ball-shaped configuration. In other embodiments, the engagement features 472a, 472b can have other suitable shapes and sizes.

As further shown in FIG. 11G, a portion of the first engagement feature 472a extends through a hole 473a defined within a first stopping member 474a and a portion of the second engagement feature 472b extends through a hole 473b defined within a second stopping member 474b. While the first and second stopping members 474a, 474b can have variety of configurations, in this illustrated embodiment the first and second stopping members 474a, 474b are in the form of second and third flanges, respectively. The second flange and the third flange each extend outward from the first flange 459 in a direction transverse to the longitudinal axis ($L_H$) of the first handle 446 and thus into the second cavity 461. As a result, each stopping member 474a, 474b is positioned between the locking ring 468 and the distal portion 463 of the coupling member 452. In other embodiments, each stopping member 474a, 474b can have other suitable configurations that allow an engagement feature to be frictionally engaged between the locking ring 468 and the distal portion 463 of the coupling member 452.

While not shown, the first engagement feature 472a is partially seated within a first channel of a set of channels 475 and the second engagement feature 472b is partially seated within a second channel of the set of channels 475. Each channel of the set of channels 475 is recessed from the outer surface 463a of the distal portion 463 of the coupling member 452, as shown in FIGS. 11E and 11F. As a result, when the first and second engagement interfaces 471a, 471b are in contact with the respective first and second engagement features 472a, 472b, a frictional engagement is formed between the locking ring 468 and the coupling member 452. This frictional engagement locks the first handle 446 and driver shaft 402 to each other. This is because the inner surface 463b of the distal portion 463 of the coupling member 452 is mated to the proximal end 448p of the driving tube 448 and the distal end 448d of the driving tube 448 is coupled to the driver shaft 402, as discussed above. Thus, inhibiting rotational movement of the coupling member 452 relative to the first handle 446 thereby locks the first handle 446 to the driver shaft 402 such that they can rotate together as a unit.

In use, the locking assembly 466 can be moved from the locked configuration to the unlocked configuration, for example, when a user actuates one of the first and second trigger elements 476, 478 to cause the locking ring 468 to shift out of frictional engagement with the first and second engagement features 472a, 472b. For sake of simplicity, the following discussion is with respect to the first trigger element 476. A person skilled in the art will understand, however, that the following discussion is also applicable to the second trigger element 478, which as shown in FIGS. 11F and 11G is structurally similar to that of the first trigger element 476.

In some embodiments, for example, a user can actuate the first trigger element 476 by applying sufficient force to its first end 476a to cause the first trigger element 476 to axially translate in a first direction (D1). As such, the first trigger element 476 is moved from its first position to a second position. This causes its second end 476b to move further into the second cavity 461 of the base member 454, thereby shifting the locking ring 468 in the first direction (D1). This shifting of the locking ring overcomes the frictional forces between the locking ring 468 and the first and second engagement features 472a, 472b. In particular, the first and second engagement features 472a, 472b are also moved in the first direction (D1) and partially received within a first recess 469a of the first set of adjacent recesses 469 and a first recess 470a of the second set of adjacent recesses 470, respectively. As a result, each engagement feature 472a, 472b is no longer frictionally engaged to the locking ring 468, and thus, the first handle 446 can rotate freely relative to the driver shaft 402 and vice versa.

To move the locking assembly 466 back into the locked configuration, the first trigger element 476 is returned to its first position. For example, in use, when the first trigger element 476 is in its second position, a user can release the first trigger element 476 causing the first biasing element 479a to expand back towards its first position. This forces the first trigger element 476 towards its first position, and as a result, the locking ring 468 shifts back into frictionally engagement with the first and second engagement features 472a, 472b.

As discussed above, when the locking assembly 466 is in its locked configuration, the first handle 446 and the driver shaft 402 can rotate together as a unit. While a user can therefore rotate the first handle 446 to effect rotation of the driver shaft 402 to drive a bone screw into bone, the user would be unable to rotate the driver shaft 402 continuously without removing his/her hand from the first handle 446. Accordingly, when the locking assembly 466 is in its unlocked configuration, the first handle 446 can be decoupled from and rotate independent of the driver shaft 402, and the first handle 446 can include a clutch assembly 480, also referred to herein as a ratchet mechanism, for allowing a user to continuously drive the driver shaft 402 in only one direction without removing their hand from the first handle 446.

Figure 11H:
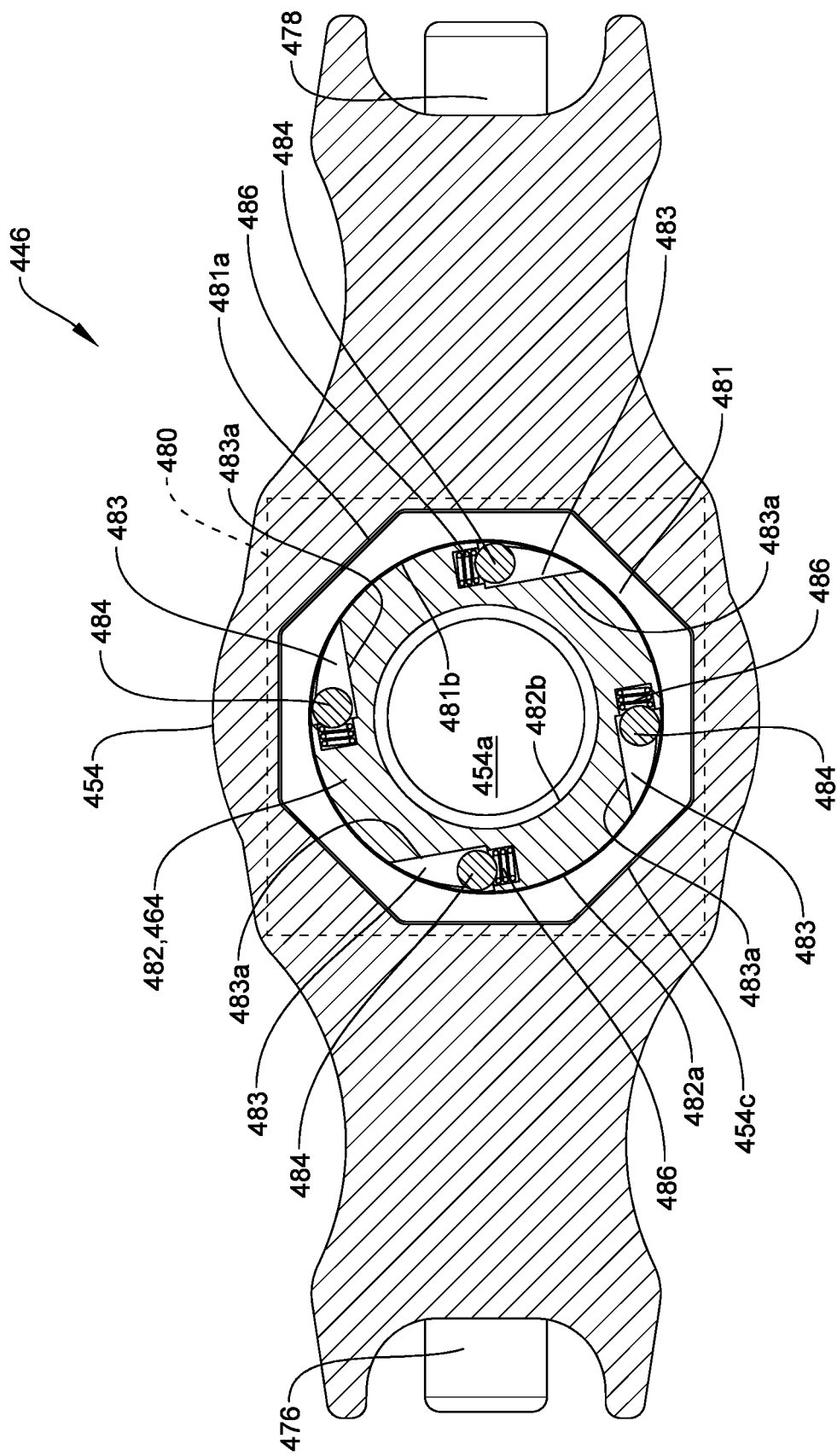
FIG. 11H is cross-sectional view of the first handle of FIG. 11B taken at 11H-11H.

The clutch assembly 480 can be configured to be selectively engaged to cause the first handle 446 to couple to and rotate with the driver shaft 402. As such, the clutch assembly 480 has an engaged configuration and a disengaged configuration. While the clutch assembly 480 can have a variety of configurations, in some embodiments, the clutch assembly 480 can be in the form of a one-way bearing. For example, in one embodiment, the clutch assembly 480, as shown in FIG. 11H, can include an outer ring 481 and an inner ring 482. In this illustrated embodiment, the inner ring 482 is also the intermediate portion 464 of the coupling member 452.

As shown in FIGS. 11E and 11F, the outer ring 481 resides within a distal portion 460a of the first cavity 460 of the base member 454, and as shown in FIG. 11H, is positioned between the inner ring 482 and an inner surface 454c of the base member 454. More specifically, an inner surface 481b of the outer ring 481 abuts the outer surface 482a of the inner ring 482, and the outer surface 481a of the outer ring 481 abuts the inner surface 454c of the base member 454 that defines the distal portion 460a of the first cavity 460. Further, the outer surface 481a of the outer ring 481 and the inner surface 454c of the base member 454 have corresponding hexagonal shapes such that the outer ring 481 is non-rotatably coupled to the base member 454. In other embodiments, the outer surface 481a and the inner surface 454c can have other suitable corresponding shapes.

As further shown in FIGS. 11E, 11F, and 11H, the inner ring 482 includes cut-out portions 483 that extend from the outer surface 482a towards the inner surface 482b thereof. The cut-out portions 483 can have any suitable shape and size. In this illustrated embodiment, each cut-out portion 483 is tubular in shape and extends inward at an angle to form a ramp interface 483a. Further, each cut-out portion 483 includes an engagement feature 484 disposed therein. In this illustrated embodiment, each engagement feature 484 is a ball-shaped element that maintains contact with the outer ring 481 via a biasing element 486 that resides within corresponding cut-out portions 483. While each biasing element 486 can have a variety of configurations, each biasing element 486, as shown in FIG. 11H, is a helical spring that biases its respective engagement feature 484 outward and in contact with the inner surface 481b of the outer ring 481.

In use, the first handle 446 can be rotated in a clockwise direction that ultimately causes it to frictionally engage with the driver shaft 402 via the clutch assembly 480 so they can rotate as a unit in the clockwise direction only to drive a bone screw into bone. More specifically, clockwise rotation of the first handle 446 causes each engagement feature 484 of the clutch assembly 480 to be pulled toward the outer ring 481 via friction. That is, the frictional forces created by the clockwise rotation of the first handle 446 force each engagement feature 484 to move radially outward along the ramp interface 483a of its respective cut-out portion 483. As a result, the friction increases between each engagement feature 484 and the outer ring 481 causing the outer ring 481 to frictionally lock to the driving tube 448, and consequently, the first handle 446 to the driver shaft 402. In this way, the first handle 446 can be rotated clockwise and counterclockwise, without the user removing his/her hand therefrom, to drive the driver shaft clockwise only, and thereby drive a bone screw into bone. Further, this can be achieved without producing an audible cue that can be confused with any other audible cues of the instrument 400.

Further, the clutch assembly 480 can inhibit back out of the implanted bone screw from bone. That is, the clutch assembly 480 can be disengaged when the first handle rotates counterclockwise. This causes the first handle 446 to decouple from the driver shaft 402 so that counterclockwise rotation of the first handle does not cause corresponding counterclockwise rotation of the driver shaft 402. In use, when the first handle 446, and thus the outer ring 481, is rotated counterclockwise, the outer ring 481 applies a frictional counterforce to the engagement features 484. This causes each engagement feature 484 to travel radially inward along the ramp interface 483a of its respective cut-out portion 483, thereby compressing the biasing element 486 in contact therewith. As such, this radial movement of each engagement feature 484 reduces its friction with the outer ring 481. As a result, the outer ring 481, and consequently the first handle 446, can therefore freely rotate in the counterclockwise direction relative to the driver shaft 402.

The clutch assembly described herein, therefore, allows the first handle to be rotated in a first direction (e.g., clockwise) to drive the driver shaft to drive a bone screw coupled thereto into bone and in a second direction (e.g., counterclockwise) in which the first handle rotates freely relative to the driver shaft. As a result, the user can maintain contact with the first handle and rotate clockwise and counterclockwise repeatedly to drive the screw in only a clockwise direction into bone. Thus, the clutching assembly allows a user to drive a bone screw into bone without removing his/her hand from the first handle.

As previously mentioned, the screw inserter instruments can be used to implant a bone screw assembly into bone. Any suitable method can be used for operating any of the screw inserter instruments having a first handle as described herein. For example, when operating the screw inserter instrument 400 (FIGS. 10A-10B), the retaining sleeve 404 can be threadably engaged with a bone screw coupled to the distal tip of the driver shaft 402, as discussed above. Once coupled to the bone screw, the second handle 450a of the stylet assembly 450 can be rotated, with the locking assembly 466 in a locked configuration and the first handle 446 held stationary, to axially translate the stylet 450b relative to the driver shaft 402. Once the stylet 450b is at a desired positioned, the stylet 450b can be docked within bone. The locking assembly 466 can be moved from its locking configuration to its unlocked configuration to decouple the first handle 446 from the driver shaft 402. This can be achieved by actuating the first or second trigger elements 476, 478 of the locking assembly 466 to move the locking ring 468 from a first position to a second position, and thus operably decouple from the driver shaft 402. When the locking assembly 466 is an unlocked configuration, the first handle 446 can be rotated in a first direction, with the second handle 450a being held stationary, to cause the first handle 446 to couple to and rotate with the driver shaft 402 to drive the bone screw into bone. This rotation can cause the outer and inner rings 481, 482 of the clutch assembly 480 to lock to one another. When the locking assembly 466 is an unlocked configuration, the first handle 446 can be rotated in a second direction relative to the driver shaft 402. Once the bone screw is driven into bone to a desired insertion depth, the retaining sleeve 404 can be unthreaded from the bone screw as described above.

The instruments disclosed herein can be designed to be disposed of after a single use, or they can be designed to be used multiple times. In either case, however, the instrument can be reconditioned for reuse after at least one use. Reconditioning can include any combination of the steps of disassembly of the instrument, followed by cleaning or replacement of particular pieces and subsequent reassembly. In particular, the instrument can be disassembled, and any number of the particular pieces or parts of the instrument can be selectively replaced or removed in any combination. Upon cleaning and/or replacement of particular parts, the instrument can be reassembled for subsequent use either at a reconditioning facility, or by a surgical team immediately prior to a surgical procedure. Those skilled in the art will appreciate that reconditioning of an instrument can utilize a variety of techniques for disassembly, cleaning/replacement, and reassembly. Use of such techniques, and the resulting reconditioned instrument, are all within the scope of the present application.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Values or ranges may be expressed herein as "about" and/or from/of "about" one particular value to another particular value. When such values or ranges are expressed, other embodiments disclosed include the specific value recited and/or from/of the one particular value to another particular value. Similarly, when values are expressed as approximations, by the use of antecedent "about," it will be understood that here are a number of values disclosed therein, and that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value or within 2% of the recited value.

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is incorporated herein only to the extent that the incorporated material does not conflict with existing definitions, statements, or other disclosure material set forth in this document. As such the disclosure as explicitly set forth herein supersedes any conflicting material incorporated herein by reference.

What is claimed is:

1. A screw inserter instrument, comprising:
   a screw drive assembly having a handle and a driver shaft coupled to the handle, the driver shaft having a distal tip configured to couple to a bone screw for driving the bone screw into bone; and
   a sleeve assembly disposed around the driver shaft, the sleeve assembly including
      a locking sleeve, and
      a retaining sleeve having a stop sleeve at least partially disposed around a distal end thereof, the stop sleeve being longitudinally fixed relative to the retaining sleeve and configured to extend distally beyond the distal tip of the driver shaft and at least partially beyond a proximal end of a bone screw coupled to the distal tip of the driver shaft to limit insertion of the bone screw into bone, the stop sleeve being rotatable independent of the coupled bone screw.

2. The screw inserter instrument of claim 1, wherein the stop sleeve is formed from at least one of a radiopaque material and an insulating material.

3. The screw inserter instrument of claim 1, wherein the stop sleeve is coupled to the locking sleeve such that rotation of the retaining sleeve causes rotation of the stop sleeve.

4. The screw inserter instrument of claim 1, wherein the retaining sleeve is rotatable independent of the stop sleeve.

5. The screw inserter instrument of claim 1, wherein the stop sleeve includes at least one window configured to allow viewing of the bone screw during coupling with the retention sleeve.

6. The screw inserter instrument of claim 1, wherein the stop sleeve extends a predetermined distance beyond the distal tip of the driver shaft, the predetermined distance being at least partially determined by a size of the bone screw engaged therewith.

7. The screw inserter instrument of claim 1, wherein the stop sleeve has an inner diameter that is greater than an outer diameter of the retaining sleeve.

8. The screw inserter instrument of claim 1, wherein the stop sleeve has a proximal end and a flared distal end, the proximal end having a diameter less than the diameter of the distal end.

9. The screw inserter instrument of claim 1, wherein the stop sleeve has a head having a substantially U-shaped configuration.

10. The screw instrument of claim 9, wherein the head comprises a base and two opposing legs extending therefrom, the head defining at least one window disposed between the two opposing legs.

11. A screw inserter system, comprising:
    a driver shaft having a distal tip configured to engage a bone screw for driving the bone screw into bone;
    a retaining sleeve disposed around the driver shaft and having a distal end configured to threadably couple with the bone screw;
    a locking sleeve disposed around the retaining sleeve; and
    a stop sleeve having a proximal end coupled to a distal end of the locking sleeve, the stop sleeve being partially disposed around a distal end of the retaining sleeve and extending distally beyond the distal tip of the driver shaft and at least partially beyond a proximal end of a bone screw coupled to the distal tip of the driver shaft, the stop sleeve being longitudinally fixed relative to the retaining sleeve and configured to limit insertion of a bone screw into bone.

12. The screw inserter system of claim 11, wherein the stop sleeve includes a distal head having a U-shaped cross section.

13. The screw inserter system of claim 11, wherein the distal end of the stop sleeve includes a head defining at least one window.

14. The screw inserter system of claim 13, wherein the at least one window is positioned to allow a user to view a bone screw coupled to the retaining sleeve.

15. The screw inserter system of claim 11, wherein the stop sleeve is fixedly coupled to the locking sleeve such that movement of the locking sleeve effects concurrent movement of the stop sleeve.

16. The screw inserter system of claim 11, wherein the stop sleeve is coupled to the locking sleeve such that the stop sleeve is configured to freely rotate relative to the locking sleeve.

* * * * *